US012721913B2

(12) United States Patent
Ludwig et al.

(10) Patent No.: US 12,721,913 B2
(45) Date of Patent: Sep. 1, 2026

(54) DR5 RADIOIMMUNOTHERAPY IN THE TREATMENT OF SOLID CANCERS

(71) Applicant: Actinium Pharmaceuticals, Inc., New York, NY (US)

(72) Inventors: Dale Ludwig, Rockaway, NJ (US); Eileen Geoghegan, Mamaroneck, NY (US)

(73) Assignee: Actinium Pharmaceuticals, Inc., New York, NY (US)

( * ) Notice: Subject to any disclaimer, the term of this patent is extended or adjusted under 35 U.S.C. 154(b) by 840 days.

(21) Appl. No.: 18/012,740

(22) PCT Filed: Jun. 23, 2021

(86) PCT No.: PCT/US2021/038626

§ 371 (c)(1),
(2) Date: Dec. 23, 2022

(87) PCT Pub. No.: WO2021/262813

PCT Pub. Date: Dec. 30, 2021

(65) Prior Publication Data

US 2023/0302168 A1 Sep. 28, 2023

Related U.S. Application Data

(60) Provisional application No. 63/042,651, filed on Jun. 23, 2020.

(51) Int. Cl.

| | |
|---|---|
| ***A61K 51/10*** | (2006.01) |
| ***A61K 45/06*** | (2006.01) |
| ***A61P 35/00*** | (2006.01) |

(52) U.S. Cl.

CPC .......... *A61K 51/1027* (2013.01); *A61K 45/06* (2013.01); *A61K 51/1093* (2013.01); *A61P 35/00* (2018.01)

(58) Field of Classification Search

CPC ................ A61K 51/1027; A61K 45/06; A61K 51/1093; A61K 31/454; A61K 31/502; A61K 31/5025; A61K 31/55; A61K 39/395; A61K 51/1096; A61P 35/00; C07K 2317/76; C07K 16/2827; C07K 16/2878

See application file for complete search history.

(56) References Cited

U.S. PATENT DOCUMENTS

| | | | |
|---|---|---|---|
| 7,834,019 | B2 | 11/2010 | Sagara et al. |
| 7,935,708 | B2 | 5/2011 | Sagara et al. |
| 8,288,396 | B2 | 10/2012 | Goto et al. |
| 8,436,004 | B2 | 5/2013 | Bamba et al. |
| 8,710,065 | B2 | 4/2014 | Tong et al. |
| 8,716,297 | B2 | 5/2014 | Woods et al. |
| 8,791,125 | B2 | 7/2014 | Sagara et al. |
| 8,796,289 | B2 | 8/2014 | Zhu et al. |
| 9,051,327 | B2 | 6/2015 | Zhu et al. |
| 9,181,239 | B2 | 11/2015 | Mastracchio |
| 9,714,244 | B2 | 7/2017 | O'Dowd et al. |
| 9,718,821 | B2 | 8/2017 | Woods et al. |
| 9,850,247 | B2 | 12/2017 | Harrison et al. |
| 10,736,975 | B2 | 8/2020 | Dave et al. |
| 2010/0113445 | A1 | 5/2010 | Deanda, Jr. et al. |
| 2016/0222459 | A1 | 8/2016 | Keating et al. |
| 2017/0021017 | A1 | 1/2017 | Chang et al. |
| 2019/0248795 | A1 | 8/2019 | Burkamp |
| 2019/0276549 | A1 | 9/2019 | De Jong et al. |
| 2019/0316203 | A1 | 10/2019 | Davison et al. |
| 2022/0125962 | A1 | 4/2022 | Ludwig et al. |

FOREIGN PATENT DOCUMENTS

| | | |
|---|---|---|
| WO | WO 2002/090360 | 11/2002 |
| WO | WO 2015/019037 | 2/2015 |
| WO | WO 2017/216559 | 12/2017 |
| WO | WO 2018/011570 | 1/2018 |

OTHER PUBLICATIONS

Atallah, E. L. et al. A Phase 2 Study of Actinium-225 (225Ac)-Lintuzumab in Older Patients with Untreated Acute Myeloid Leukemia (AML)—Interim Analysis of 1.5 μci/Kg/Dose. Blood 132, 1457-1457 (2018).

Banerjee, S. R. et al. Evaluation of 111 In-DOTA-5D3, a Surrogate SPECT Imaging Agent for Radioimmunotherapy of Prostate-Specific Membrane Antigen. J. Nucl. Med. 60, 400-406 (2019).

Bavi, P. et al. Prognostic significance of TRAIL death receptors in Middle Eastern colorectal carcinomas and their correlation to oncogenic KRAS alterations. Mol. Cancer 9, (2010).

Borchardt, P. E., Yuan, R. R., Miederer, M., McDevitt, M. R. & Scheinberg, D. A. Targeted Actinium-225 in Vivo Generators for Therapy of Ovarian Cancer. Cancer Res. 63, 5084-5090 (2003).

Chen, H. et al. Integrin α v β 3-targeted radionuclide therapy combined with immune checkpoint blockade immunotherapy synergistically enhances anti-tumor efficacy. Theranostics 9, 7948-7960 (2019).

Demaria, S. et al. Immune-mediated inhibition of metastases after treatment with local radiation and CTLA-4 blockade in a mouse model of breast cancer. Clin. Cancer Res. 11, 728-34 (2005).

Forero-Torres, A. et al. TBCRC 019: A Phase II Trial of Nanoparticle Albumin-Bound Paclitaxel with or without the Anti-Death Receptor 5 Monoclonal Antibody Tigatuzumab in Patients with Triple-Negative Breast Cancer. Clin. Cancer Res. 21, 2722-9 (2015).

Gantcn, T. M. ct al. Prognostic significancc of tumour nccrosis factor-rclatcd apoptosis-inducing ligand (TRAIL) rcccptor exprcssion in paticnts with brcast canccr. J. Mol. Mcd. 87, 995-1007 (2009).

Garelli, E. et al. Abscopal effect in lung cancer: three case reports and a concise review. Immunotherapy 11, 1445-1461 (2019).

(Continued)

*Primary Examiner* — Robert S Cabral

(74) *Attorney, Agent, or Firm* — Dentons Cohen & Grigsby, P.C.; Michael E. Dukes

(57) ABSTRACT

Methods for treating a proliferative disease or disorder by administering an antibody radio-conjugate alone or in combination with an immune checkpoint therapy such as an antibody against an immune checkpoint inhibitor, and/or a DNA damage response inhibitor. The proliferative disease or disorder may be a solid cancer, such as breast cancer, ovarian cancer, or prostate cancer.

14 Claims, 1 Drawing Sheet

(56) References Cited

OTHER PUBLICATIONS

Gelmon, et al., Olaparib in Patients With Recurrent High-Grade Serous or Poorly Differentiated Ovarian Carcinoma or Triple-Negative Breast Cancer: A Phase 2, Multicentre, Open-Label, Non-Randomized Study. Lancet Oncol. 12:852-61 (2011).
Grasselly, C. et al. The Antitumor Activity of Combinations of Cytotoxic Chemotherapy and Immune Checkpoint Inhibitors is Model-Dependent. Front. Immunol. 9, 1-13 (2018).
Hiniker, S. M. et al. A Prospective Clinical Trial Combining Radiation Therapy With Systemic Immunotherapy in Metastatic Melanoma. Int. J. Radiat. Oncol. Biol. Phys. 96, 578-88 (2016).
Jiao, R., Allen, K. J. H., Malo, M. E., Rickles, D. & Dadachova, E. Evaluating the Combination of Radioimmunotherapy and Immunotherapy in a Melanoma Mouse Model. Int. J. Mol. Sci. 21, 773 (2020).
Jutzy, J. M. S., Lemons, J. M., Luke, J. J. & Chmura, S. J. The Evolution of Radiation Therapy in Metastatic Breast Cancer: From Local Therapy to Systemic Agent. Int. J. Breast Cancer 2018, 1-7 (2018).
Kaur, P. et al. A mouse model for triple-negative breast cancer tumor-initiating cells (TNBC-TICs) exhibits similar aggressive phenotype to the human disease. BMC Cancer 12, 120 (2012).
Krishnakumar and Kraus, The PARP Side of the Nucleus: Molecular Actions, Physiological Outcomes, and Clinical Targets. Mol. Cell 39 (1) 8-24 (2010).
Lamichhane, P., Amin, N., Agarwal, M. & Lamichhane, N. Checkpoint Inhibition: Will Combination with Radiotherapy and Nanoparticle-Mediated Delivery Improve Efficacy? Medicines 5, 114 (2018).
Macher-Goeppinger, S. et al. Prognostic value of tumor necrosis factor-related apoptosis-inducing ligand (TRAIL) and TRAIL receptors in renal cell cancer. Clin. Cancer Res. 15, 650-659 (2009).
Min, Y. J. et al. Prognostic significance of Fas (CD95) and TRAIL receptors (DR4/DR5) expression in acute myelogenous leukemia. Leuk. Res. 28, 359-365 (2004).
Mortland, L. ct al. Clinical Significancc of CD33 Nonsynonymous Singlc-Nuclcotidc Polymorphisms in Pcdiatric Paticnts with Acutc Mycloid Lcukcmia Trcated with Gcmtuzumab-Ozogamicin-Containing Chemotherapy. Clin. Cancer Res. 19, 1620-1627 (2013).
Murai, J., et al., Trapping of PARPI and PARP2 by Clinical PARP Inhibitors. Cancer Res. 72, 5588-5599 (2012).
Murai, J., et al., Stereospecific PARP Trapping by BMN 673 and Comparison with Olaparib and Rucaparib. Mol Cancer Ther. 13 (2), 433-443 (2014).
Naoum, G. E., Buchsbaum, D. J., Tawadros, F., Farooqi, A. & Arafat, W. O. Journey of TRAIL from Bench to Bedside and its Potential Role in Immuno-Oncology. Oncol. Rev. 11, 332 (2017).
Oei, A. L. et al. Enhancing the abscopal effect of radiation and immune checkpoint inhibitor therapies with magnetic nanoparticle hyperthermia in a model of metastatic breast cancer. Int. J. Hyperth. 36, 47-63 (2019).
Pedersen, M. H. et al. Downregulation of antigen presentation-associated pathway proteins is linked to poor outcome in triple-negative breast cancer patient tumors. Oncoimmunology 6, e1305531 (2017).
Pouget, J. P. et al. Clinical radioimmunotherapy—the role of radiobiology. Nat. Rev. Clin. Oncol. 8, 720-734 (2011).
Reits, E. A. et al. Radiation modulates the peptide repertoire, enhances MHC class I expression, and induces successful antitumor immunotherapy. J. Exp. Med. 203, 1259-1271 (2006).
Rodriguez-Ruiz, M. E. et al. Abscopal Effects of Radiotherapy are Enhanced by Combined Immunostimulatory mAbs and are Dependent on CD8 T Cells and Crosspriming. Cancer Res. 76, 5994-6005 (2016).
Schmid, P. et al. Atezolizumab and Nab-Paclitaxel in Advanced Triple-Negative Breast Cancer. N. Engl. J. Med. 379, 2108-2121 (2018).
Sharabi, A. B., Lim, M., DeWeese, T. L. & Drake, C. G. Radiation and checkpoint blockade immunotherapy: radiosensitisation and potential mechanisms of synergy. Lancet. Oncol. 16, e498-509 (2015).
Sharma, S. K. et al. A rapid bead-based radioligand binding assay for the determination of target-binding fraction and quality control of radiopharmaceuticals. Nucl. Med. Biol. 71, 32-38 (2019).
Song, H. et al. Radioimmunotherapy of Breast Cancer Metastases with Alpha-Particle Emitter 225Ac: Comparing Efficacy with 213Bi and 90Y. Cancer Res. 69, 8941-8948 (2009).
Spierings, D. C. et al. Tissue distribution of the death ligand TRAIL and its receptors. J. Histochem. Cytochem. 52, 821-31 (2004).
Takeda, K. et al. Combination Therapy of Established Tumors by Antibodies Targeting Immune Activating and Suppressing Molecules. J. Immunol. 184, 5493-5501 (2010).
Takeda, K. et al. Induction of Tumor-specific T Cell Immunity by Anti-DR5 Antibody Therapy. J. Exp. Med. 199, 437-448 (2004).
Tutt, et al., Oral poly(ADP-ribose) Polymerase Inhibitor Olaparib in Patients With BRCA1 or BRCA2 Mutations and Advanced Breast Cancer: A Proof-of-Concept Trial. Lancet. 376:235-244 (2010).
Twyman-Saint Victor, C. et al. Radiation and dual checkpoint blockade activate non-redundant immune mechanisms in cancer. Nature 520, 373-377 (2015).
Uno, T. et al. Eradication of established tumors in mice by a combination antibody-based therapy. Nat. Med. 12, 693-698 (2006).
Vanpouillc-Box, C. ct al. DNA cxonuclcasc Trcxl rcgulatcs radiothcrapy-induccd tumour immunogcnicity. Nat. Commun. 8, 15618 (2017).
Wilson, N. S. et al. An Fcγ receptor-dependent mechanism drives antibody-mediated target-receptor signaling in cancer cells. Cancer Cell 19, 101-113 (2011).
Woodhouse BC, Dianova II, Parsons JL, Dianov GL.. Poly(ADP-ribose) polymerase-1 modulates DNA repair capacity and prevents formation of DNA double strand breaks. DNA Repair (Amst) 7: 932-940 (2008).
Xu, L. et al. Combinatorial surrobody libraries. Proc. Natl. Acad. Sci. USA. 105, 10756-10761 (2008).
Zhang, B. et al. Mislocalization of death receptors correlates with cellular resistance to their cognate ligands in human breast cancer cells. Oncotarget 3, (2012).
Zhang, L. & Fang, B. Mechanisms of resistance to TRAIL-induced apoptosis in cancer. Cancer Gene Ther. 12, 228-237 (2005).
International Search Report and Written Opinion dated Nov. 17, 2021 for corresponding PCT Application No. PCT/US2021/038626.
Burvenich et al., "Molecular Imaging of Death Receptor 5 Occupancy and Saturation Kinetics in Vivo by Humanized Monoclonal Antibody CS-1008", (Nov. 2013), Clinical Cancer Research, vol. 19, No. 21.
Oliver et al., "Treatment of Human Colon Cancer Xenografts with TRA-8 Anti-death Receptor 5 Antibody Alone or in Combination with CPT-11", (Apr. 2008), Clinical Cancer Research, vol. 17, No. 7.

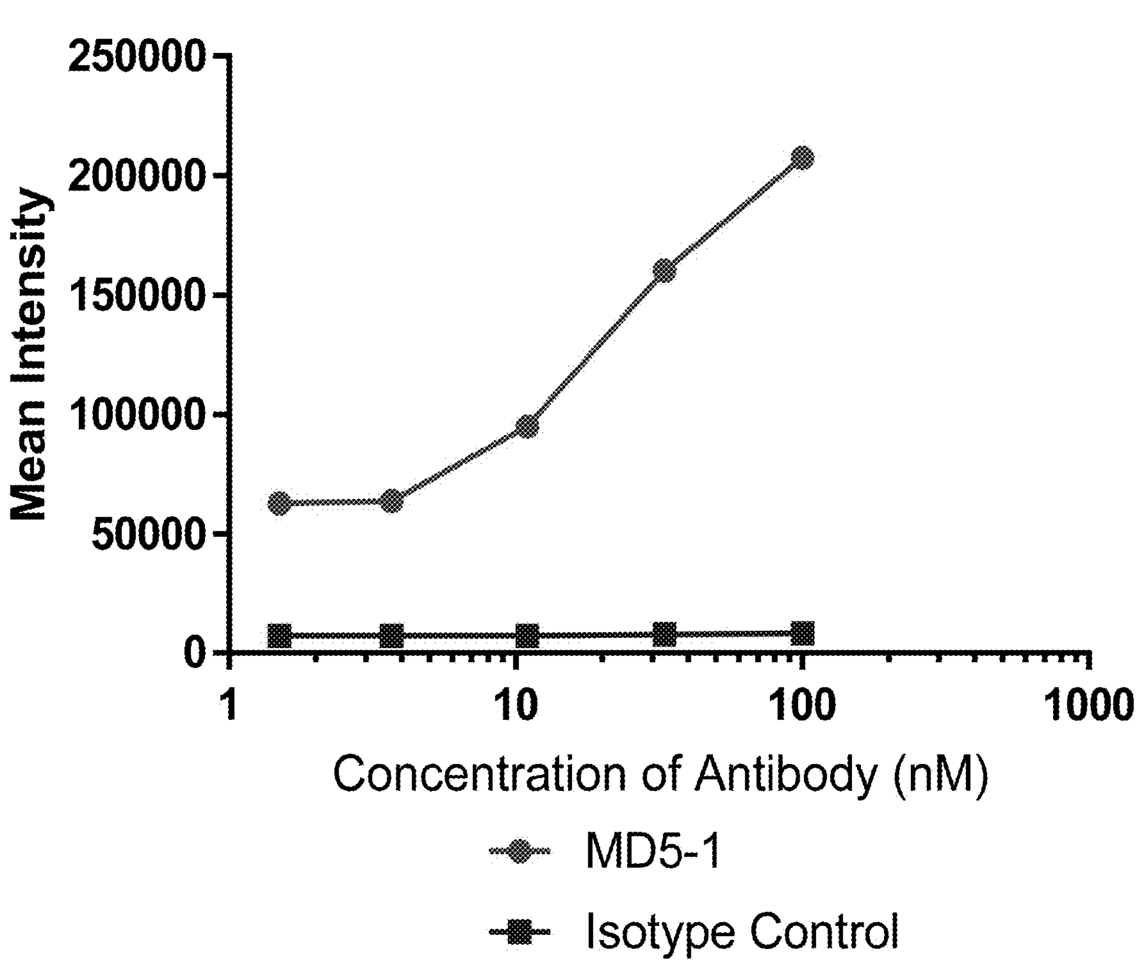
MD5-1 binding to 4T1 cell line
250000
200000
150000
100000
50000
0
Mean Intensity
1
10
100
1000
Concentration of Antibody (nM)
MD5-1
Isotype Control

DR5 RADIOIMMUNOTHERAPY IN THE TREATMENT OF SOLID CANCERS

CROSS-REFERENCE TO RELATED APPLICATIONS

This present application is a U.S. national stage filing under 35 U.S.C. § 371 of International Application No. PCT/US2021/038626, filed on Jun. 23, 2021, which claims the benefit under 35 U.S.C. § 119(e) of prior U.S. Provisional Application Ser. No. 63/042,651, filed Jun. 23, 2020, the content of which is incorporated herein in its entirety.

FIELD

The present disclosure relates to methods for treating a subject having cancer by administration of a DR5 radioimmunotherapy, either alone or in combination with immune checkpoint therapies or PARP inhibitors.

BACKGROUND

Humans express two functional death receptors (DR4 and DR5), also known as tumor necrosis factor-related apoptosis-inducing ligand receptors 1 and 2 (TRAIL-R1 and -R2), which become upregulated on cell surfaces as part of an immune surveillance mechanism to alert the immune system of the presence of virally infected or transformed cells. TRAIL, the ligand that binds death receptors, is expressed on immune cells such as T-cells and NK cells, and upon engagement of DR4 or DR5, TRAIL trimerizes the death receptor and induces an apoptotic cascade that is independent of p53 (Naoum, et al.). While DR4 and DR5 can be found expressed at low levels in some normal tissues (Spierings, et al.), they are upregulated on the surface of many tumor tissues including renal, lung, acute myeloid leukemia (AML), cervical, and breast cancers (Naoum, et al.; Spierings, et al.; Ganten, et al.; Macher-Goeppinger, et al.).

Following the identification of death receptors as a viable therapeutic target, many DR4 and DR5-targeting antibodies and recombinant TRAIL (rTRAIL) proteins have been developed and evaluated clinically, relying mechanistically on induction of apoptosis through direct engagement and trimerization of DR4 or DR5 (rTRAIL) or death receptor clustering through Fc γ receptor mediated engagement (DR4/5 targeting antibodies; Wilson, et al.). Examples of DR4- or DR5-targeting antibodies that have been evaluated clinically include mapatumumab, conatumumab, lexatumumab, tigatuzumab, drozitumab, and LBY-135. Generally, the results demonstrated that these targeted approaches were safe but not clinically effective, with limited induction of apoptosis in tumor cells (Naoum, et al.). As such, further clinical development has largely been halted.

To further explore the potential clinical development of a DR5-targeting antibody, tigatuzumab was evaluated in a Phase 2 clinical trial in triple negative breast cancer (TNBC) patients. Forero-Torres, et al., confirmed the expression of DR5 on both primary and metastatic tumor samples, demonstrating that DR5 is a suitable target for directing therapeutic intervention in this cancer type and metastatic disease. Additionally, Ganten, et al., found that DR5 expression was associated with higher tumor grade, higher Ki67 index, and positive nodal status at diagnosis and negatively correlated with overall survival in breast cancer patients. Tigatuzumab was evaluated in combination with albumin-bound paclitaxel in a randomized Phase 2 trial in TNBC, and although the adverse event profile was favorable, no clinical benefit was observed (Forero-Torres, et al.).

Despite disappointing clinical results with DR5-targeting antibodies in TNBC, the expression profile of DR5 in TNBC and many other cancers remains attractive for targeting with an armed antibody, such as an antibody radio-conjugate (ARC). In treatment regimens targeting solid tumors, such as breast cancer, radiation is typically used only to treat the site of the primary tumor after surgical resection, and is only used palliatively for metastases (Jutzy, et al.). An alternative approach to achieve targeted delivery of radiation to both primary and metastatic tumors and to spare normal tissues from radiation toxicity is through use of an ARC. ARCs combine the targeting specificity of an antibody with the potent cell-killing and immunostimulatory effects of radiation. Since many DR5-targeting antibodies have been tested clinically and found to be safe, this suggests such a strategy may be amenable to targeting with an ARC.

Accordingly, improved therapies for the treatment of cancer using anti-DR5 ARCs and compositions comprising those anti-DR5 ARCs are desired.

Immune Checkpoint Therapies

Cancer cells have developed means to evade the standard checkpoints of the immune system. For example, cancer cells have been found to evade immunosurveillance through reduced expression of tumor antigens, downregulation of MHC class I and II molecules leading to reduced tumor antigen presentation, secretion of immunosuppressive cytokines such as TGFb, recruitment or induction of immunosuppressive cells such as regulatory T cells (Treg) or myeloid-derived suppressor cells (MDSC), and overexpression of certain ligands [e.g., programmed death ligand-1 (PD-L1)] that inhibit the host's existing antitumor immunity.

Another major mechanism of immune suppression by cancer cells is a process known as "T-cell exhaustion", which results from chronic exposure to tumor antigens, and is characterized by the upregulation of inhibitory receptors. These inhibitory receptors serve as immune checkpoints in order to prevent uncontrolled immune reactions. Various immune checkpoints acting at different levels of T cell immunity have been described in the literature, including PD-1 (i.e., programmed cell death protein 1) and its ligands PD-L1 and PD-L2, CTLA-4 (i.e., cytotoxic T-lymphocyte associated protein-4) and its ligands CD80 and CD86, LAG3 (i.e., Lymphocyte-activation gene 3), B and T lymphocyte attenuator, TIGIT (T-cell immunoreceptor with Ig and ITIM domains), TIM-3 (i.e., T-cell immunoglobulin and mucin-domain containing protein 3), and VISTA (V-domain immunoglobulin suppressor of T cell activation).

Enhancing the efficacy of the immune system by therapeutic intervention is a particularly exciting development in cancer treatment. As indicated, checkpoint inhibitors such as CTLA-4 and PD-1 prevent autoimmunity and generally protect tissues from immune collateral damage. In addition, stimulatory checkpoints, such as OX40 (i.e., tumor necrosis factor receptor superfamily, member 4; TNFR-SF4), CD137 (i.e., TNFR-SF9), GITR (i.e., Glucocorticoid-Induced TNFR), CD27 (i.e., TNFR-SF7), CD40 (i.e., cluster of differentiation 40), and CD28, activate and/or promote the expansion of T-cells. Regulation of the immune system by inhibition or overexpression of these proteins is an area of promising current research.

Thus, a promising therapeutic strategy across various cancers is the use of immune checkpoint therapies that may remove some of blockades on the immune system used by cancer cells. For example, antibodies against certain immune checkpoint inhibitors (ICI) may block interaction between checkpoint inhibitor proteins and their ligands, therefore preventing the signaling events that would otherwise have led to inhibition of an immune response against the tumor cell. The recent approval of the anti-PD-L1 ICI antibody atezolizumab in 2019 represents an important new development in the treatment paradigm for TNBC patients. Unfortunately, a large percentage of patients do not respond to this treatment, with only 56% of patients demonstrating a clinical response in the Phase 3 IMpassion130 clinical trial (Schmid, et al.).

One strategy to improve response rates that is being widely investigated is combination treatment with ICI antibodies and radiation therapy. Improved outcomes may occur due to the wide array of immunomodulatory effects of radiation treatment that can turn immunologically "cold" tumors "hot," thereby improving the recognition of tumor cells by the immune system. Specifically, radiation is known to upregulate expression of MHC class I, calreticulin, Fas, TRAIL receptors, and NKG2DL. When combined with the direct cell-killing effect of radiation, this creates an immunostimulatory environment that improves T cell infiltration, dendritic cell cross-presentation, and can lead to improved immune-mediated tumor control (Sharabi, et al.).

There is a growing body of preclinical evidence supporting the ability of radiation to synergize with ICI antibodies, and this is also being explored in the clinic with increasing numbers of clinical trials evaluating the combination of external beam radiation with immune checkpoint therapies across various tumor types and ICI antibodies (Lamichhane, et al.). Clinical evidence supporting this combination has been generated in melanoma, with two studies demonstrating a clinical benefit using radiation in combination with the anti-cytotoxic T-lymphocyte-associated protein 4 (CTLA-4) ICI antibody, ipilmumab (Twyman-Saint Vistor, et al.; Hiniker, et al.).

Accordingly, therapies for the treatment of cancer using an ARC in combination with one or more immune checkpoint therapies, such as an ICI antibody, are desired.

PARP Inhibitors

Inhibitors of the DNA repair protein "PARP" (poly(ADP-ribose) polymerase), referred to individually and collectively as "PARPi", have been approved for use in breast and ovarian cancer, particularly in patients having BRCA1/2 mutations. BRCA1 and 2 function in homologous recombination repair (HRR). When mutated, they induce genomic instability by shifting the DNA repair process from conservative and precise HRR to non-fidelitous methods such as DNA endjoining, which can produce mutations via deletions and insertions.

PARPi have been shown to exhibit synthetic lethality, as exhibited by potent single agent activity, in BRCA1/2 mutant cells. This essentially blocks repair of single-strand DNA breaks. Since HRR is not functional in these tumor cells, cell death results. Because most tumors do not carry BRCA1 or BRCA2 mutations, the potency of PARPi in such tumors is far less pronounced.

The efficacy of PARPi in ovarian cancer and breast cancer patients who have loss-of-function mutations in BRCA1 or BRCA2 genes is largely attributed to the genetic concept of synthetic lethality: that proteins of BRCA 1 and 2 normally maintain the integrity of the genome by mediating a DNA repair process, known as homologous recombination (HR); and PARPi causes a persistent DNA lesion that, normally, would otherwise be repaired by HR. In the presence of PARPi, PARP1 is trapped on DNA which stalls progression of the replication fork. This stalling is cytotoxic unless timely repaired by the HR system. In cells lacking effective HR, they are unable to effectively repair these DNA lesions, and thus die.

Mutations in BRCA genes and others in the HR system are not prevalent in many cancer types. So, to better harness the therapeutic benefits of PARPi in such cancers, one can induce "artificial" synthetic lethality by pairing a PARPi with either chemotherapy or radiation therapy. Preclinical studies have demonstrated that combining radiation therapy and PARPi can increase the sensitivity of BRCA1/2 mutant tumor cells to PARP inhibition and extend the sensitivity of non-mutant BRCA tumors to PARP inhibition. Additional studies have shown that ionizing radiation (IR) itself can mediate PARPi synthetic lethality in tumor cells.

Accordingly, therapies for cancer comprising safer more effective methods to deliver ionizing radiation in combination with a PARPi are desired.

SUMMARY OF THE INVENTION

The present disclosure provides improved methods for the treatment of cancer, and in particular solid tumors, in a subject by administration of an antibody radio-conjugate (ARC) alone or in combination with an immune checkpoint therapy and/or one or more DNA damage response inhibitors (DDRi). An exemplary DDRi includes at least one or more antibodies or small molecules targeting poly(ADP-ribose) polymerase (i.e., a poly(ADP-ribose) polymerase inhibitor or PARPi). Such combination therapies may enhance the efficacy of the immune checkpoint therapy and/or DDRi through selective targeting of ionizing radiation to specific cancer cells, such as those in both primary and metastatic TNBC tumors.

Accordingly, the present disclosure relates to methods for treating a subject having cancer comprising administering to the subject an ARC that targets cancer cells in the subject, wherein the amount of the ARC is therapeutically effective.

The present disclosure further relates to methods for treating a subject having cancer comprising administering to the subject (i) either or both of an immune checkpoint therapy and a DDRi in conjunction with (ii) an ARC that targets cancer cells in the subject, wherein the amounts of the immune checkpoint therapy and/or DDRi and the ARC, when administered in conjunction with one another, are therapeutically effective.

According to certain aspects, the cancer is a solid tumor.

According to certain aspects, the solid tumor is a breast cancer, ovarian cancer, prostate cancer, lung cancer, squamous cell carcinoma of the head and neck, gastric cancer, pancreatic cancer, brain cancer (e.g., glioblastoma and neuroblastoma), liver cancer, sarcoma and melanoma.

According to certain preferred aspects, the solid tumor is a breast cancer, such as a triple negative breast cancer, ovarian cancer, or prostate cancer.

According to certain aspects, the antibody radio-conjugate comprises an antibody or small molecule that targets DR5 (DR5 targeting agent).

According to certain aspects, the DR5 targeting agent may comprise an alpha-emitting isotope or a beta-emitting isotope.

According to certain aspects, the antibody radio-conjugate comprises $^{225}$Ac-anti-DR5, $^{213}$Bi-anti-DR5, $^{227}$Th-anti-DR5, $^{212}$Pb-anti-DR5, $^{211}$At-anti-DR5, $^{177}$Lu-anti-DR5, $^{90}$Y-anti-DR5, $^{131}$I-anti-DR5, $^{67}$Cu-anti-DR5, or a combination thereof.

According to certain preferred aspects, the antibody radio-conjugate comprises $^{225}$ Ac-anti-DR5, $^{177}$Lu-anti-DR5, or $^{131}$I-anti-DR5.

According to certain aspects, the immune checkpoint therapy may comprise an antibody against CTLA-4, PD-1, TIM-3, VISTA, BTLA, LAG-3, TIGIT, CD28, OX40, GITR, CD137, CD40, CD40L, CD27, HVEM, PD-L1, PD-L2, PD-L3, PD-L4, CD80, CD86, CD137-L, GITR-L, CD226, B7-H3, B7-H4, BTLA, TIGIT, GALS, KIR, 2B4, CD160, CGEN-15049, or a combination thereof.

According to certain aspects, the immune checkpoint therapy may comprise an antibody against an immune checkpoint inhibitor (ICI).

According to certain aspects, the ICI antibody may be selected from the group consisting of an antibody against PD-1, PD-L1, PD-L2, CTLA-4, and a combination thereof.

According to certain aspects, the DDRi is a PARPi, such as a PARPi selected from the group consisting of olaparib, niraparib, rucaparib, talazoparib, and a combination thereof.

According to certain aspects, the antibody radio-conjugate may be provided in a subject effective amount comprising a total protein content of less than 16 mg/kg body weight of the subject, less than 10 mg/kg body weight of the subject, or less than 6 mg/kg body weight of the subject.

According to certain aspects, the antibody radio-conjugate may be provided in a total radioactivity content of 0.1 to 10 uCi/kg body weight of the subject, such as 0.2 to 6 uCi/kg body weight of the subject, or 0.4 to 5 uCi/kg body weight of the subject for $^{225}$ Ac-containing ARCs; or may be provided in a total radioactivity content of 10 mCi to 500 mCi, or 10 mCi to 200 mCi, or 0.1 to 3 mCi/kg body weight of the subject for $^{131}$I-containing ARCs; or may be provided in a total radioactivity content of less than 500 uCi/kg body weight of the subject, such as 5 uCi/kg to 450 uCi/kg body weight of the subject, or 20 to 250 uCi/kg body weight of the subject for $^{177}$Lu-containing ARCs.

According to certain aspects, the ICI antibody may be provided in a subject effective amount comprising a dose of 0.1 mg/kg to 50 mg/kg of the patient's body weight, such as 0.1-5 mg/kg, or 5-30 mg/kg.

According to certain aspects, the PARPi may be provided in a subject effective amount comprising 0.1 mg/day-1200 mg/day, such as 0.100 mg/day-600 mg/day, or 0.25 mg/day-1 mg/day. Exemplary subject effective amounts include 0.1 mg, 0.25 mg, 0.5 mg, 0.75 mg, 1.0 mg, 100 mg, 200 mg, 300 mg, 400 mg, 500 mg, 600 mg, 700 mg, 750 mg, 800 mg, 900 mg, and 1000 mg, taken orally in one or two doses per day.

The objects of the present disclosure will be realized and attained by means of the combinations specifically outlined in the appended claims. The foregoing general description and the following detailed description and examples are provided to illustrate various aspects of the present disclosure, and by no means are to be viewed as limiting any of the described embodiments.

BRIEF DESCRIPTION OF THE DRAWING

FIG. 1 shows expression levels of mouse DR5 on 4T1 tumor cells, a commonly used TNBC tumor model.

DETAILED DESCRIPTION

The methods disclosed herein use targeted ionizing radiation directed against tumor necrosis factor-related apoptosis-inducing ligand receptors 2 (TRAIL-R2, also known as death receptor 5 or DR5), such as provided by a radiolabeled anti-DR5 antibody, to mediate induction of apoptosis in DR5+ tumor types such as breast cancer, ovarian cancer, prostate cancer, lung cancer, squamous cell carcinoma of the head and neck, gastric cancer, pancreatic cancer, brain cancer (e.g., glioblastoma and neuroblastoma), liver cancer, sarcoma and melanoma. According to certain preferred aspects, the DR5+ tumor types is a breast cancer, such as a triple negative breast cancer, ovarian cancer, or prostate cancer.

The methods disclosed herein further use targeted ionizing radiation in synergistic combination with an immune checkpoint therapy, such as an antibody against an immune checkpoint inhibitor (ICI antibodies), and/or with a poly (ADP-ribose) polymerase inhibitors (PARPi). The targeted ionizing radiation, provided by an antibody radioconjugate (ARC), such as the radiolabeled anti-DR5 antibody, may be effective across a broad range of cancer and tumor types, and particularly in primary and metastatic breast cancers such as triple negative breast cancer (TNBC), ovarian cancer, and prostate cancer.

Definitions and Abbreviations

Unless otherwise defined herein, scientific and technical terms used in connection with the present invention shall have the meanings that are commonly understood by those of ordinary skill in the art. Additionally, in this description and in the appended claims, use of the singular includes the plural and plural encompasses the singular, unless specifically stated otherwise. For example, although reference is made herein to "an" antibody, "a" tumor, and "the" radiolabel, one or more of any of these components and/or any other components described herein may be used.

The word "comprising" and forms of the word "comprising", as used in this description and in the claims, does not limit the present invention to exclude any variants or additions. Additionally, although the present invention has been described in terms of "comprising", the processes, materials, and compositions detailed herein may also be described as consisting essentially of or consisting of. For example, while certain aspects of the invention have been described in terms of a method comprising administering an effective amount of an ARC and an effective amount of an immune checkpoint therapy and/or a DDRi, a method "consisting essentially of" or "consisting of" administering an effective amount of an ARC and an effective amount of an immune checkpoint therapy and/or a DDRi is also within the present scope. In this context, "consisting essentially of" means that any additional components will not materially affect the efficacy of the method.

Moreover, other than in the examples, or where otherwise indicated, all numbers expressing, for example, quantities of ingredients used in the specification are to be understood as being modified in all instances by the term "about". Accordingly, unless indicated to the contrary, the numerical parameters set forth in the following specification are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques. Thus, the term "about" when used before a numerical designation, e.g., temperature, time, amount, and concentration, including a range, indicates approximations which may vary by ±10%, ±5%, or ±1%.

As used herein, "administer", with respect to a targeting agent such as an antibody, antibody fragment, Fab fragment, or aptamer, means to deliver the agent to a subject's body via any known method suitable for antibody delivery. Specific modes of administration include, without limitation, intravenous, transdermal, subcutaneous, intraperitoneal, intrathecal and intra-tumoral administration. Exemplary administration methods for antibodies may be as substantially described in International Publication No. WO 2016/187514, incorporated by reference herein.

In addition, in this disclosure, antibodies or antibody fragments can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

As used herein, and unless specifically indicated otherwise, the term "antibody" includes, without limitation, (a) an immunoglobulin molecule comprising two heavy chains and two light chains and which recognizes an antigen; (b) polyclonal and monoclonal immunoglobulin molecules; (c) monovalent and divalent fragments thereof (e.g., di-Fab), and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring (e.g., IgG-Fc-silent). Furthermore, antibodies include chimeric antibodies, wholly synthetic antibodies, single chain antibodies, and fragments thereof. Antibodies may be human, humanized or nonhuman.

As used herein, "Immunoreactivity" refers to a measure of the ability of an immunoglobulin to recognize and bind to a specific antigen. "Specific binding" or "specifically binds" or "binds" refer to an antibody binding to an antigen or an epitope within the antigen with greater affinity than for other antigens. Typically, the antibody binds to the antigen or the epitope within the antigen with an equilibrium dissociation constant ($K_D$) of about $1\times10^{-7}$M or less, for example about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a nonspecific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), Pan troglodytes (chimpanzee, chimp) or Callithrix jacchus (common marmoset, marmoset).

As used herein, an "anti-DR5 antibody" is an antibody, antibody fragment, peptide, surrobody, Fab fragment, or aptamer that binds to any available epitope of DR5. According to certain aspects, the anti-DR5 antibody is a human or humanized antibody against DR5. According to certain aspects, the anti-DR5 antibody binds to an epitope of DR5 recognized by the any of mapatumumab, conatumumab, lexatumumab, tigatuzumab, drozitumab, and LBY-135. According to certain aspects, the anti-DR5 antibody is selected from the group comprising mapatumumab, conatumumab, lexatumumab, tigatuzumab, drozitumab, and LBY-135.

According to certain aspects, the anti-DR5 antibody is a surrobody that targets both DR5 and DR4. "Surrobodies" are structurally similar to antibodies, comprising both the variable and constant regions of the heavy chain(s), and in place of a pair of identical variable light chains, two distinct peptide segments that are bound to one another noncovalently: (i) VpreB1 (CD179A), which is coded by prelymphocyte gene 1 (VPREB1), and (ii) immunoglobulin 2-5 polypeptide 1 (CD179B; 25). Variations are introduced into the sequences of both VpreB1 and λ5, thereby producing pre-BCR-like structures with greater diversity than antibodies (Xu, et al.). One such surrobody that targets both DR5 and DR4 has been developed by Sea Lane Biotechnologies (i.e., i2P45, also known as SL-466).

An "epitope" refers to the target molecule site (e.g., at least a portion of an antigen) that is capable of being recognized by, and bound by, a targeting agent such as an antibody, antibody fragment, Fab fragment, or aptamer. For a protein antigen, for example, this may refer to the region of the protein (i.e., amino acids, and particularly their side chains) that is bound by the antibody. Overlapping epitopes include at least one to five common amino acid residues. Methods of identifying epitopes of antibodies are known to those skilled in the art and include, for example, those described in Antibodies, A Laboratory Manual, Cold Spring Harbor Laboratory, Ed Harlow and David Lane (1988).

As used herein, the terms "proliferative disorder" and "cancer" may be used interchangeably and may include, without limitation, a solid cancer (e.g., a tumor). "Solid cancers" include, without limitation, bone cancer, pancreatic cancer, skin cancer, cancer of the head or neck, cutaneous or intraocular malignant melanoma, uterine cancer, ovarian cancer, prostate cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, pediatric tumors, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally-induced cancers including those induced by asbestos.

According to certain aspects, the solid cancer may be breast cancer, ovarian cancer, prostate cancer, lung cancer, squamous cell carcinoma of the head and neck, gastric cancer, pancreatic cancer, brain cancer (e.g., glioblastoma and neuroblastoma), liver cancer, sarcoma and melanoma. According to certain preferred aspects, the solid cancer is a breast cancer, such as a triple negative breast cancer, ovarian cancer, or prostate cancer.

The antibody radio-conjugates disclosed herein comprises an antibody against DR5 labeled with a radioisotope. As used herein, a "radioisotope" can be an alpha-emitting isotope, a beta-emitting isotope, and/or a gamma-emitting isotope. Preferred are $^{225}$Ac, $^{213}$Bi, $^{227}$Th, $^{212}$Pb, $^{211}$At, $^{177}$Lu, $^{90}$Y, $^{131}$I, $^{67}$Cu, or combinations thereof.

The ARC may be an antibody radiolabeled with $^{225}$Ac ("$^{225}$Ac-labeled"), and the effective amount may be below, for example, 5.0 μCi/kg (i.e., where the amount of $^{225}$Ac administered to the subject delivers a radiation dose of below 5.0 uCi per kilogram of subject's body weight). According to certain aspects, when the antibody is $^{225}$Ac-labeled, the effective amount is below 4.5 μCi/kg, 4.0 μCi/kg, 3.5 μCi/kg, 3.0 μCi/kg, 2.5 μCi/kg, 2.0 μCi/kg, 1.5

μCi/kg, 1.0 μCi/kg, 0.9 μCi/kg, 0.8 μCi/kg, 0.7 μCi/kg, 0.6 μCi/kg, 0.5 μCi/kg, 0.4 μCi/kg, 0.3 μCi/kg, 0.2 μCi/kg, 0.1 μCi/kg or 0.05 μCi/kg. According to certain aspects, when the antibody is $^{225}$ Ac-labeled, the effective amount is from 0.05 μCi/kg to 0.1 μCi/kg, from 0.1 μCi/kg to 0.2 μCi/kg, from 0.2 μCi/kg to 0.3 μCi/kg, from 0.3 μCi/kg to 0.4 μCi/kg, from 0.4 μCi/kg to 0.5 μCi/kg, from 0.5 μCi/kg to 0.6 μCi/kg, from 0.6 μCi/kg to 0.7 μCi/kg, from 0.7 μCi/kg to 0.8 μCi/kg, from 0.8 μCi/kg to 0.9 μCi/kg, from 0.9 μCi/kg to 1.0 μCi/kg, from 1.0 μCi/kg to 1.5 μCi/kg, from 1.5 μCi/kg to 2.0 μCi/kg, from 2.0 μCi/kg to 2.5 μCi/kg, from 2.5 μCi/kg to 3.0 μCi/kg, from 3.0 μCi/kg to 3.5 μCi/kg, from 3.5 μCi/kg to 4.0 μCi/kg, from 4.0 μCi/kg to 4.5 μCi/kg, or from 4.5 μCi/kg to 5.0 μCi/kg. According to certain aspects, when the antibody is $^{225}$ Ac-labeled, the effective amount is 0.05 μCi/kg, 0.1 μCi/kg, 0.2 μCi/kg, 0.3 μCi/kg, 0.4 μCi/kg, 0.5 μCi/kg, 0.6 μCi/kg, 0.7 μCi/kg, 0.8 μCi/kg, 0.9 μCi/kg, 1.0 μCi/kg, 1.5 μCi/kg, 2.0 μCi/kg, 2.5 μCi/kg, 3.0 μCi/kg, 3.5 μCi/kg, 4.0 μCi/kg or 4.5 μCi/kg.

According to certain aspects, when the ARC is $^{225}$Ac-labeled, the therapeutically effective amount of comprises a single dose that delivers less than 12Gy, or less than 8 Gy, or less than 6 Gy, or less than 4 Gy, or less than 2 Gy, such as doses of 2 Gy to 8 Gy, to the subject.

The ARC may be an antibody radiolabeled with $^{177}$Lu ("$^{177}$Lu labeled"), and the effective may be below, for example, 1 mCi/kg (i.e., where the amount of $^{177}$Lu-labeled antibody administered to the subject delivers a radiation dose of below 1000 μCi per kilogram of subject's body weight). According to certain aspects, when the antibody is $^{177}$Lu-labeled, the effective amount is below 900 μCi/kg, 800 μCi/kg, 700 μCi/kg, 600 μCi/kg, 500 μCi/kg, 400 μCi/kg, 300 μCi/kg, 200 μCi/kg, 150 μCi/kg, 100 μCi/kg, 80 μCi/kg, 60 μCi/kg, 50 μCi/kg, 40 μCi/kg, 30 μCi/kg, 20 μCi/kg, 10 μCi/kg, 5 μCi/kg, or 1 μCi/kg. According to certain aspects, the effective amount of the $^{177}$Lu-labelled antibody is 1 μCi/kg, 2.5 μCi/kg, 5 μCi/kg, 10 μCi/kg, 20 μCi/kg, 30 μCi/kg, 40 μCi/kg, 50 μCi/kg, 60 μCi/kg, 70 μCi/kg, 80 μCi/kg, 90 μCi/kg, 100 μCi/kg, 150 μCi/kg, 200 μCi/kg, 250 μCi/kg, 300 μCi/kg, 350 μCi/kg, 400 μCi/kg or 450 μCi/kg. According to certain aspects, an $^{177}$Lu-labeled antibody may be administered at a dose that includes any combination of upper and lower limits as described herein, such as from at least 50 μCi/kg to below 1 mCi/kg, or from at least 100 μCi/kg to below 1 mCi/kg.

According to certain aspects, the effective amount of the $^{177}$Lu labeled antibody may be from 1 mCi to 200 mCi, such as from 5 mCi to 100 mCi, or 10 mCi to 150 mCi, or 50 mCi to 200 mCi. According to aspects, the effective therapeutic amount of the $^{177}$Lu-labeled antibody may be from 200 mCi to 800 mCi, such as from 200 mCi to 600 mCi, or 400 mCi to 600 mCi, or 200 mCi to 300 mCi, or 300 mCi to 400 mCi, or 400 mCi to 500 mCi, or 500 mCi to 600 mCi, or 600 mCi to 700 mCi, 700 mCi to 800 mCi.

The ARC may be an antibody radiolabeled with iodine-131 ($^{131}$I-labelled), and the effective amount of $^{131}$I-labelled antibody may be below, for example, 2 mCi/kg. According to certain aspects, the effective amount of the $^{131}$I-labelled antibody is below 1.8 mCi/kg, 1.6 mCi/kg, 1.4 mCi/kg, 1.2 μCi/kg, 1.0 μCi/kg, 900 μCi/kg, 800 μCi/kg, 700 μCi/kg, 600 μCi/kg, 500 μCi/kg, 400 μCi/kg, 300 μCi/kg, 200 μCi/kg, 100 μCi/kg, 80 μCi/kg, 60 μCi/kg, 40 μCi/kg, 20 μCi/kg, 10 μCi/kg, 5 μCi/kg, or 2 μCi/kg.

According to aspects, the effective amount of the $^{131}$I-labelled antibody is from 2 μCi/kg to 10 μCi/kg, 10 μCi/kg to 20 μCi/kg, 20 μCi/kg to 40 μCi/kg, from 40 μCi/kg to 60 μCi/kg, from 60 μCi/kg to 80 μCi/kg, from 80 μCi/kg to 100 μCi/kg, from 100 μCi/kg to 200 μCi/kg, from 200 μCi/kg to 300 μCi/kg, from 300 μCi/kg to 400 μCi/kg, from 400 μCi/kg to 500 μCi/kg, from 500 μCi/kg to 600 μCi/kg, from 600 μCi/kg to 700 μCi/kg, from 700 μCi/kg to 800 μCi/kg, from 800 μCi/kg to 900 μCi/kg, from 900 μCi/kg to 1 mCi/kg, from 1 mCi/kg to 1.1 mCi/kg, from 1.1 mCi/kg to 1.2 mCi/kg, from 1.2 mCi/kg to 1.3 mCi/kg, from 1.3 mCi/kg to 1.4 mCi/kg, or from 1.4 mCi/kg to 1.5 mCi/kg.

According to aspects, the effective amount of the $^{131}$I-labelled antibody is from 10 mCi to 400 mCi, such as from 20 mCi to 400 mCi, 10 mCi to 300 mCi, or 20 mCi to 300 mCi, or 10 mCi to 200 mCi, or 20 mCi to 200 mCi, or 20 mCi to 150 mCi.

While select radionuclide labels have been disclosed herein, any from the list provided above are contemplated for labeling the antibodies of the ARC.

The majority of the targeting agent (antibody, antibody fragment, etc.) administered to a subject typically consists of non-labeled targeting agent, with the minority being the labeled targeting agent, such as with any of the labels described herein. The ratio of labeled to non-labeled targeting agent can be adjusted using known methods. Thus, the ARC may be provided in a total protein amount of up to 100 mg, such as up to 60 mg, such as 5 mg to 45 mg, or a total protein amount of between 0.01 mg/kg patient weight to 15.0 mg/kg patient weight, such as between 0.01 mg/kg patient weight to 1.0 mg/kg, or between 0.01 mg/kg patient weight to 0.5 mg/kg, or 0.01 mg/kg patient weight to 0.2 mg/kg, or 0.2 mg/kg patient weight to 0.6 mg/kg patient weight, or 0.3 mg/kg patient weight, or 0.4 mg/kg patient weight, or 0.5 mg/kg patient weight.

According to certain aspects, the radiolabeled antibody comprises the labeled fraction and non-labeled fraction in a ratio of labeled: non-labeled of from about 0.01:10 to 1:10, such as 0.01:5 to 0.1:5, or 0.01:3 to 0.1:3, or 0.01:1 to 0.1:1 labeled: non-labeled. Moreover, the radiolabeled antibody may be provided as a single dose composition tailored to a specific patient. See for example administration methods disclosed in International Publication No. WO 2016/187514, incorporated by reference herein in its entirety. According to certain aspects, the radiolabeled antibody may be provided in multiple doses, wherein each dose in the regime may comprise a composition tailored to a specific patient.

This inventive combination of a labeled fraction and a non-labeled fraction of the antibody or other biologic delivery vehicle allows the composition to be tailored to a specific patient, wherein each of the radiation dose and the protein dose of the antibody are personalized to that patient based on at least one patient specific parameter. As such, each vial of the composition may be made for a specific patient, where the entire content of the vial is delivered to that patient in a single dose. When a treatment regime calls for multiple doses, each dose may be formulated as a patient specific dose in a vial to be administered to the patient as a "single dose" (i.e., full contents of the vial administered at one time). The subsequent dose may be formulated in a similar manner, such that each dose in the regime provides a patient specific dose in a single dose container.

As used herein, the term "subject" includes, without limitation, a mammal such as a human, a non-human primate, a dog, a cat, a horse, a sheep, a goat, a cow, a rabbit, a pig, a rat and a mouse. Where the subject is human, the subject can be of any age. For example, the subject can be 60 years or older, 65 or older, 70 or older, 75 or older, 80 or older, 85 or older, or 90 or older. Alternatively, the subject can be 60 years or younger, 55 years or younger, 50 years or younger, 45 or younger, 40 or younger, 35 or younger, 30 or younger, 25 or younger, or 20 or younger. For a human subject afflicted with cancer, the subject can be newly diagnosed, or relapsed and/or refractory, or in remission.

As used herein, "treating" a subject afflicted with a cancer shall include, without limitation, (i) slowing, stopping or reversing the cancer's progression, (ii) slowing, stopping or reversing the progression of the cancer's symptoms, (iii) reducing the likelihood of the cancer's recurrence, and/or (iv) reducing the likelihood that the cancer's symptoms will recur. According to certain preferred aspects, treating a subject afflicted with a cancer means (i) reversing the cancer's progression, ideally to the point of eliminating the cancer, and/or (ii) reversing the progression of the cancer's symptoms, ideally to the point of eliminating the symptoms, and/or (iii) reducing or eliminating the likelihood of relapse (i.e., consolidation, which ideally results in the destruction of any remaining cancer cells).

"Therapeutically effective amount" or "effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient, reduction in a tumor burden, arrested or slowed growth of a tumor, and/or absence of metastasis of cancer cells to other locations in the body. According to certain aspects, "therapeutically effective amount" or "effective amount" refers to an amount of the antibody that may deplete or cause a reduction in the overall number of cells expressing the antigen to which the antibody is targeted or reacts or may inhibit growth of cells expressing the antigen.

The term "immune checkpoint therapy" refers to a molecule capable of modulating the function of an immune checkpoint protein in a positive or negative way (in particular the interaction between an antigen presenting cell (APC) such as a cancer cell and an immune T effector cell). The term "immune checkpoint" refers to a protein directly or indirectly involved in an immune pathway that under normal physiological conditions is crucial for preventing uncontrolled immune reactions and thus for the maintenance of self-tolerance and/or tissue protection. The one or more immune checkpoint therapies described herein may independently act at any step of the T cell-mediated immunity including clonal selection of antigen-specific cells, T cell activation, proliferation, trafficking to sites of antigen and inflammation, execution of direct effector function and signaling through cytokines and membrane ligands. Each of these steps is regulated by counterbalancing stimulatory and inhibitory signals that fine tune the response.

In the context of the present disclosure, the term immune checkpoint therapy encompasses therapies such as antibodies capable of down-regulating at least partially the function of an inhibitory immune checkpoint (antagonist) and/or up-regulating at least partially the function of a stimulatory immune checkpoint (agonist). As example, an immune checkpoint therapy may refer to an antibody against an immune checkpoint inhibitor (ICI) that may be upregulated in certain cancers, and thus may inhibit the function of the ICI.

The term "DDRi" refers to an inhibitor of a DNA damage response pathway protein, of which a PARPi is an example. The term "PARPi" refers to an inhibitor of poly(ADP-ribose) polymerase. In the context of the present invention, the term PARPi encompasses molecules that may bind to and inhibitor the function of poly(ADP-ribose) polymerase, such as antibodies, peptides, or small molecules.

As used herein, administering to a subject either or both of an immune checkpoint therapy and a DDRi "in conjunction with" an ARC that targets cancer cells in the subject means administering the immune checkpoint therapy and/or DDRi before, during and/or after administration of the ARC. This administration includes, without limitation, the following scenarios: (i) the immune checkpoint therapy and/or DDRi is administered first, and the ARC is administered second; (ii) the immune checkpoint therapy and/or DDRi is administered concurrently with the ARC (e.g., the DDRi is administered orally once per day for n days, and the ARC is administered intravenously in a single dose on one of days 0 through n−1 of the DDRi regimen or in multiple doses starting on day 0, 1, or 2, with administration every 1, 2, 3, 4, 5, 6, 7, or 8 days and extending up to day n−1, n, or n+1 of the DDRi regimen); (iii) the immune checkpoint therapy and/or DDRi is administered concurrently with the ARC on alternating days (e.g., the DDRi is administered orally once per days every 1, 2, 3, or 4 days for a duration of greater than one week, such as orally once per day for 14 days, 21 days, 28 days, 35 days, 42 days, 49 days, or a longer period during which the cancer being treated does not progress and during which the DDRi does not cause unacceptable toxicity, and the ARC is administered intravenously in a single dose within the first month of the DDRi regimen on a day that the DDRi is not administered, or the ARC is administered in multiple doses on days that the DDRi is not administered such as DDRi on D1, D3, D5 and ARC on DO, D2, D4 etc,); and (iv) the ARC is administered first (e.g., intravenously in a single dose or a plurality of doses over a period of days or weeks), and the immune checkpoint therapy and/or DDRi is administered second (e.g., the DDRi is administered orally once per day for 14 days, 21 days, 28 days, 35 days, 42 days, 49 days, or a longer period during which the cancer being treated does not progress and during which the DDR inhibitor does not cause unacceptable toxicity). Additional permutations are provided below in the Examples section.

"Pharmaceutically acceptable salt" refers to acid addition salts of basic compounds, e.g., those compounds including a basic amino group, and to basic salts of acidic compounds, e.g., those compounds including a carboxyl group, and to amphoteric salts of compounds that include both an acidic and a basic moiety, such that these salts are suitable for administration in vivo, preferably to humans. Various organic and inorganic acids may be used for forming acid addition salts. Pharmaceutically acceptable salts are derived from a variety of organic and inorganic counter ions well known in the art. Pharmaceutically acceptable salts include, when the molecule contains a basic functionality, by way of example only, hydrochloride, hydrobromide, tartrate, mesylate, acetate, maleate, oxalate and the like, and when the molecule contains an acidic functionality, by way of example only, sodium, potassium, calcium, magnesium, ammonium, tetraalkylammonium, N-methylmorpholinium, and the like. In one embodiment, the pharmaceutically acceptable salt of ezatiostat is ezatiostat hydrochloride.

"Synergistic combinations," as used herein, are combinations of monotherapies that may provide a therapeutic effect that is comparable to the effectiveness of a monotherapy, while reducing adverse side effects, e.g. damage to non-targeted tissues, immune status, and other clinical indicia. Alternatively, synergistic combinations may provide for an improved effectiveness, which may be measured by total tumor cell number, length of time to relapse, and other indicia of patient health. Synergistic combinations of the present disclosure combine an ARC and an immune checkpoint therapy (e.g., an antibody against an ICI), a DDRi (e.g., antibody or small molecule inhibitor of PARP), or combination of an immune checkpoint therapy and a DDRi.

An "article of manufacture" indicates a package containing materials useful for the treatment, prevention and/or diagnosis of the disorders described herein. The article of manufacture may comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a DR5 targeting agent, such as any of the anti-DR5 antibodies disclosed herein.

A "label" or "package insert" is used to refer to instructions customarily included in commercial packages of therapeutic products that contain information about the indications, usage, dosage, administration, combination therapy, contraindications and/or warnings concerning the use of such therapeutic products. As used herein, a label may indicate that the composition is used for treating a solid cancer, such as a breast cancer, triple negative breast cancer, ovarian cancer, or prostate cancer, and may optionally indicate administration routes and/or methods. Moreover, the article of manufacture may comprise (a) a first container with a composition contained therein, wherein the composition comprises at least the DR5 targeting agent; and (b) a second container with a composition contained therein, wherein the composition comprises a further cytotoxic or otherwise therapeutic agent according to aspects of the presently disclosed invention. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Throughout this application, various publications are cited. The disclosure of these publications is hereby incorporated by reference into this application to describe more fully the state of the art to which this invention pertains.

Although methods and materials similar or equivalent to those described herein can be used in the practice or testing described herein, suitable methods and materials are described below.

Antibody Radio-Conjugates (ARCs)

Prior work in the field has demonstrated that while DR5 is expressed on both primary and metastatic tumor samples, clinical therapies comprising administration of a DR5 targeting agent alone or in combination with a chemotherapeutic provided no clinical benefit (Naoum, et al., Forero-Torres, et al.). While use of a DR5 targeting agent in an antibody drug-conjugate (ADC) is a possible alternative approach, the present inventors believed that an ARC presented several advantages over an ADC for targeting DR5. One of the mechanisms of resistance to DR5-targeting antibody therapy in breast cancer cell lines is reduced surface expression (Zhang, et al.). ARCs are less sensitive to surface antigen expression levels than naked antibodies or ADCs due to the potency of the ionizing radiation from the radionuclide. As an example, $^{225}$Ac-lintuzumab, which targets CD33, has been shown to exhibit clinical activity in acute myeloid leukemia (AML) patients heterozygous for a single nucleotide polymorphism (SNP) that effects CD33 splicing and has been shown to reduce surface levels of full length CD33 (Atallah, et al.). The CD33-targeting antibody drug conjugate, Mylotarg, has no clinical benefit in this CD33 SNP heterozygous population (Mortland, et al.).

Together, these studies suggested that an ARC is a superior modality for targeting antigens with low or variable expression levels. Further, tumor cells are capable of evading induction of apoptosis through DR5 engagement via anti-DR5 antibodies by modulating the expression levels of apoptotic cascade proteins (including FADD, Bcl-2, and Bax; Zhang, et al. (2005)). The dsDNA damage caused by the ARC may bypass the apoptotic signaling pathway used to mediate TRAIL/DR5-induced apoptosis, thereby eliminating the tumor cells' ability to evade TRAIL-mediated apoptosis.

The present inventors realized that an ARC utilizing an alpha-emitting radioisotope, such as Actinium-225 ($^{225}$Ac), would be particularly attractive for this approach. $^{225}$Ac emits four high linear energy transfer alpha particles over its decay profile, over a very short distance of about 3-4 cells' thickness (Pouget, et al.), making them very potent in effecting lethal double-strand DNA breaks by direct ionizing radiation, but also much safer to handle compared to beta-emitting isotopes. $^{225}$Ac-based ARCs have been used clinically to target hematopoietic cancers, including the CD33-targeting ARC $^{225}$Ac-lintuzumab that is currently being developed as a therapeutic for acute myeloid leukemia (AML).

Comparison of the potency and efficacy of a Her2-targeting monoclonal antibody (mAb) conjugated and labeled with different radionuclide warheads: $^{225}$Ac (emits 4 alpha particles), Yttrium-90 ($^{90}$Y, a beta-emitter) or Bismuth-213 ($^{213}$Bi, emits 1 alpha particle). While the $^{213}$Bi ARC did significantly improve survival compared to controls, all $^{213}$Bi ARC-treated mice did succumb to the tumor. The $^{225}$Ac ARC was the only compound that effected a dramatic reduction in the development of lung metastases resulting in 8 of 12 mice achieving a sustained complete response (CR; Song, et al.).

Finally, one of the mechanisms of immune escape identified in TNBC is downregulation of proteins in the MHC class I antigen presentation pathway (Pedersen, et al.). Since radiation is known to improve peptide presentation and upregulate expression of MHC class I (Reits, et al.), targeted delivery of radiation to both primary and metastatic TNBC cells with an ARC is a promising strategy that has the potential to improve immune-mediated control of tumors alone, and particularly in combination with an immune checkpoint therapy.

Accordingly, ARCs of the present disclosure include antibodies against DR5 that are labeled with $^{225}$Ac, $^{213}$Bi, $^{227}$Th, $^{212}$Pb, $^{211}$At, $^{177}$Lu, $^{90}$Y, $^{131}$I, $^{67}$Cu, or combinations thereof, wherein the antibodies may be recombinant, monoclonal, chimeric, humanized, human, or a fragment thereof. Exemplary antibodies against DR5 include at least tigatuzumab (CD-1008) from Daiichi Sankyo, conatumumab (AMG 655) from Amgen, mapatumumab from AstraZeneca, lexatumumab (also known as ETR2-ST01) from Creative Biolabs, LBY-135, and drozitumab from Genentech. Initial studies in mouse models may use the surrogate mouse antibody TRA-8 or MD5-1. Moreover, the ARC may comprise a surrobody that targets DR5, such as the surrobody i2P45 that targets DR4 and DR5 developed by Sea Lane Technologies).

The ARC may include antibodies that are multi-specific. For example, the ARC may include bispecific antibodies against any two different tumor-specific antigens, or two different epitopes of the same antigen. As example, the ARC may comprise a multi-specific antibody against a first epitope of DR5 and a second epitope of DR5, or against an epitope of DR5 and epitopes of one or more additional different antigens, such as an antigen selected from DR4, CD33, HER2, HER3.

Alternatively, the present disclosure contemplates methods which include administration of more than one ARC. For example, the ARC may comprise a first antibody and at least a second antibody, wherein the first and second antibodies recognize different epitopes of the same antigen or different antigens. For example, the ARC may comprise a first antibody against at least one epitope of DR5, and a second antibody against a different epitope of DR5 than the first antibody, or against an epitope of a different antigen, such as an antigen selected from the list presented above.

ARC—Radiolabeling

The ARCs include antibodies labeled with a radioisotope, such as $^{225}$Ac, so that on treatment of a patient with the ARC, the radionuclide becomes localized to cells expressing the antigen, i.e., DR5, and induces damage to, and potentially kills, those cells. In addition to the many mechanisms by which antibodies may kill cells, emission of ionizing radiation from a radionuclide labeled antibody may kill cells in close proximity to the antibody bound antigen expressing cells. The radionuclide emits radioactive particles which can damage cellular DNA to the point where the cellular repair mechanisms are unable to allow the cell to continue living. Thus, if the antigen expressing cells are involved in a tumor, the radionuclide may beneficially kill the tumor cells.

The antibodies may be labeled with the radionuclide by any means known in the art. Methods for affixing a radioisotope to an antibody (i.e., "labeling" an antibody with a radioisotope) are known and described, such as in International Publication No. WO 2017/155937, incorporated herein in its entirety.

According to one aspect, the radionuclide may be attached or chelated by a chelating agent which is conjugated to the antibody such as substantially described in WO 2019/027973, incorporated herein by reference in its entirety. That is, the radionuclide labeled antibody may be prepared by first forming a chelator conjugated antibody ("conjugated antibody"), and then chelating a radionuclide with the conjugated antibody to form the radiolabeled antibody. A radionuclide may be chelated by the conjugated antibody at any time following conjugation.

Useful chelators include compounds which have the dual functionality of sequestering metal ions plus the ability to covalently bind a biological carrier such as an antibody. Numerous chelators are known in the art. Exemplary chelators suitable for use in the present compositions and methods include, but are not limited to, chelators such as S-2-(4-Isothiocyanatobenzyl)-1,4,7,10 tetraazacyclododecanetetraacetic acid (p-SCN-Bn-DOTA), diethylene triamine pentaacetic acid (DTPA); ethylene diamine tetraacetic acid (EDTA); 1,4,7,10-tetraazacyclododecane-N,N',N",N"'-tetraacetic acid (DOTA); p-isothiocyanatobenzyl-1,4,7,10-tetraazacyclododecane-1,4,7,10-the-traacetic acid (p-SCN-Bz-DOTA); 1,4,7,10-tetraazacyclododecane-N,N',N"-triacetic acid (DO3A); 1,4,7,10-tetraazacyclododecane-1,4,7,10-tetrakis(2-propionic acid) (DOTMA); 3,6,9-triaza-12-oxa-3,6,9-tricarboxymethylene-10-carboxy-13-phenyl-tridecanoic acid ("B-19036"); 1,4,7-triazacyclononane-N,N',N"-triacetic acid (NOTA); 1,4,8,11-tetraazacyclotetradecane-N,N',N",N"'-tetraacetic acid (TETA); triethylene tetraamine hexaacetic acid (TTHA); trans-1,2-diaminohexane tetraacetic acid (CYDTA); 1,4,7,10-tetraazacyclododecane-1-(2-hydroxypropyl)-4,7,10-triacetic acid (HP-DO3A); trans-cyclohexane-diamine tetraacetic acid (CDTA); trans (1,2)-cyclohexane dietylene triamine pentaacetic acid (CDTPA); 1-oxa-4,7,10-triazacyclododecane-N,N',N"-triacetic acid (OTTA); 1,4,7,10-tetra-azacyclododecane-1,4,7,10-tetrakis {3-(4-carboxyl)-butanoic acid}; 1,4,7,10-tetra-azacyclododecane-1,4,7,10-tetrakis(acetic acid-methyl amide); 1,4,7,10-tetra-azacyclododecane-1,4,7,10-tetrakis(methylene phosphonic acid); and derivatives thereof.

The radiolabeled antibody may be stable for a time period long enough to produce and administer to a patient (e.g., several days or weeks), but the radionuclide may decay the antibody after it has reached the target cells (cells expressing the antigen) and before it can exert damage to normal cells. For example, it has been found that greater than 75% of a $^{225}$ Ac labeled monoclonal antibody against CD33 may remain intact after storage for 24 hours at 4° C. This provides enough time to produce, transport, and administer the ARC, and enough time for the radionuclide to damage the target cells. The $^{225}$ Ac labeled anti-CD33 is then decayed before it significantly damages cells not expressing the CD33 antigen.

The radiolabeled antibody may be prepared as a composition by the methods disclosed in the International Patent Application Publication No. WO2016/187514. Moreover, the radiolabeled antibody may be administered by methods disclosed in the same publication.

The antibody may be labeled with $^{225}$ Ac, $^{177}$Lu, or $^{131}$I, and may be at least 5-fold, 10-fold, 20-fold, 50-fold, or even 100-fold more effective at causing cell death of than a control antibody, wherein the control antibody comprises an un-labeled antibody against the same epitope or antigen as the radiolabeled antibody.

Combination Therapy—ARC and Immune Checkpoint Inhibitor Antibodies

One of the mechanisms of immune escape identified in TNBC is downregulation of proteins in the MHC class I antigen presentation pathway (Pedersen, et al.). Since radiation is known to improve peptide presentation and upregulate expression of MHC class I (Reits, et al.), the preset inventors believed that targeted delivery of radiation to both primary and metastatic tumors with an ARC would be a promising strategy with potential to improve immune-mediated control of tumors in combination with immune checkpoint therapies.

Moreover, given the large body of clinical evidence investigating the expression profile and safety of targeting DR5 and the potential for radiation to synergize with immune checkpoint therapies, the present inventors hypothesized that DR5 would a suitable target for an ARC strategy in the treatment of cancers.

Immune checkpoint therapies of the present disclosure include molecules that totally or partially reduce, inhibit, interfere with or modulate one or more checkpoint proteins. Checkpoint proteins regulate T-cell activation or function. Immune checkpoint therapies may unblock an existing immune response inhibition by binding to or otherwise disabling checkpoint inhibition. The immune checkpoint therapies may include monoclonal antibodies, humanized antibodies, fully human antibodies, antibody fragments, small molecule therapeutics, or a combination thereof.

Exemplary immune checkpoint therapies may specifically bind to and inhibit a checkpoint protein, such as the inhibitory receptors CTLA-4, PD-1, TIM-3, VISTA, BTLA, LAG-3 and TIGIT, and/or the activating receptors CD28, OX40, CD40, GITR, CD137, CD27, and HVEM. Additionally, the immune checkpoint therapy may bind to a ligand of any of the aforementioned checkpoint proteins, such as PD-L1, PD-L2, PD-L3, and PD-L4 (ligands for PD-1); CD80 and CD86 (ligands for CTLA-4); CD137-L (ligand of CD137); and GITR-L (ligand of GITR). Other exemplary immune checkpoint therapies may bind to checkpoint proteins such as CD226, B7-H3, B7-H4, BTLA, TIGIT, GALS, KIR, 2B4 (belongs to the CD2 family of molecules and is expressed on all NK, γδ, and memory CD8+ (αβ) T cells), CD160 (also referred to as BY55), and CGEN-15049.

Central to the immune checkpoint process are the CTLA-4 and PD-1 immune checkpoint pathways. The CTLA-4 and PD-1 pathways are thought to operate at different stages of an immune response. CTLA-4 is considered the "leader" of the immune checkpoint inhibitors (ICI), as it stops potentially autoreactive T cells at the initial stage of naive T-cell activation, typically in lymph nodes. The PD-1 pathway regulates previously activated T cells at the later stages of an immune response, primarily in peripheral tissues. Moreover, progressing cancer patients have been shown to lack upregulation of PD-L1 by either tumor cells or tumor-infiltrating immune cells. Immune checkpoint therapies targeting the PD-1 pathway might thus be especially effective in tumors where this immune suppressive axis is operational and reversing the balance towards an immune protective environment would rekindle and strengthen a pre-existing anti-tumor immune response. PD-1 blockade can be accomplished by a variety of mechanisms including antibodies that bind PD-1 or its ligand, PD-L1.

For example, the immune checkpoint therapy may comprise an inhibitor of the PD-1 checkpoint, which may decrease, block, inhibit, abrogate, or interfere with signal transduction resulting from the interaction of PD-1 with one or more of its binding partners, such as PD-L1 and PD-L2. The inhibitor of the PD-1 checkpoint may be an anti-PD-1 antibody, antigen binding fragment, fusion proteins, oligopeptides, and other molecules that decrease, block, inhibit, abrogate or interfere with signal transduction resulting from the interaction of PD-1 with PD-L1 and/or PD-L2. In some embodiments, a PD-1 checkpoint inhibitor reduces the negative co-stimulatory signal mediated by or through cell surface proteins expressed on T lymphocytes so as render a dysfunctional T-cell less dysfunctional (e.g., enhancing effector responses to antigen recognition). In some embodiments, the PD-1 checkpoint therapy is an anti-PD-1 antibody.

Thus, the immune checkpoint therapy may comprise a monoclonal antibody against an immune checkpoint inhibitor (ICI) such as against CTLA-4, PD-1, or PD-L1.

According to certain aspects, the ICI antibody may be an antibody against PD-1. The ICI antibody may be an anti-PD-1 antibody, such as nivolumab. For example, the inhibitors of PD-1 biological activity (or its ligands) disclosed in U.S. Pat. No. 7,029,674. Exemplary antibodies against PD-1 include: Anti-mouse PD-1 antibody Clone J43 (Cat #BE0033-2) from BioXcell; Anti-mouse PD-1 antibody Clone RMP1-14 (Cat #BE0146) from BioXcell; mouse anti-PD-1 antibody Clone EH12; Merck's MK-3475 anti-mouse PD-1 antibody (Keytruda®, pembrolizumab, lambrolizumab); and AnaptysBio's anti-PD-1 antibody, known as ANB011; antibody MDX-1 106 (ONO-4538); Bristol-Myers Squibb's human IgG4 monoclonal antibody nivolumab (Opdivo®, BMS-936558, MDX1106); AstraZeneca's AMP-514, and AMP-224; and Pidilizumab (CT-011), CureTech Ltd.

According to certain aspects, the immune checkpoint therapy is an inhibitor of PD-L1. Exemplary inhibitors of PD-L1 include antibodies (e.g., an anti-PD-L1 antibody, i.e., ICI antibody), RNAi molecules (e.g., anti-PD-L1 RNAi), antisense molecules (e.g., an anti-PD-L1 antisense RNA), dominant negative proteins (e.g., a dominant negative PD-L1 protein), and small molecule inhibitors. An exemplary anti-PD-L1 antibody includes clone EH12. Exemplary antibodies against PD-L1 include: Genentech's MPDL3280A (RG7446); anti-mouse PD-L1 antibody Clone 10F.9G2 (Cat #BE0101) from BioXcell; anti-PD-L1 monoclonal antibody MDX-1105 (BMS-936559) and BMS-935559 from Bristol-Meyer's Squibb; MSB0010718C; mouse anti-PD-L1 Clone 29E.2A3; and AstraZeneca's MEDI4736 (Durvalumab).

According to certain aspects, the immune checkpoint therapy is an inhibitor of PD-L2 or may reduce the interaction between PD-1 and PD-L2. Exemplary inhibitors of PD-L2 include antibodies (e.g., an anti-PD-L2 antibody, i.e., ICI antibody), RNAi molecules (e.g., an anti-PD-L2 RNAi), antisense molecules (e.g., an anti-PD-L2 antisense RNA), dominant negative proteins (e.g., a dominant negative PD-L2 protein), and small molecule inhibitors. Antibodies include monoclonal antibodies, humanized antibodies, deimmunized antibodies, and Ig fusion proteins.

According to certain aspects, the immune checkpoint therapy may be an inhibitor of CTLA-4, such as an anti-CTLA-4 antibody, i.e., ICI antibody. According to one aspect, the ICI antibody may be ipilimumab. The anti-CTLA-4 antibody may block the binding of CTLA-4 to CD80 (B7-1) and/or CD86 (B7-2) expressed on antigen presenting cells. Exemplary antibodies against CTLA-4 include: Bristol Meyers Squibb's anti-CTLA-4 antibody ipilimumab (also known as Yervoy®, MDX-010, BMS-734016 and MDX-101); anti-CTLA4 Antibody, clone 9H10 from Millipore; Pfizer's tremelimumab (CP-675,206, ticilimumab); and anti-CTLA-4 antibody clone BNI3 from Abcam. According to certain aspects, the immune checkpoint inhibitor may be a nucleic acid inhibitor of CTLA-4 expression.

According to certain aspects, the immune checkpoint therapy may include more than one modulator of an immune checkpoint protein, such as one or more ICI antibodies. Thus, the immune checkpoint therapy may comprise a first antibody or inhibitor against a first ICI and a second antibody or inhibitor against a second ICI. For example, a first inhibitor may be an antibody against PD-1 and the second inhibitor may be an antibody against CTLA-4, or PD-L1, or PD-L2.

Combination Therapy—ARC and DDRi

The additional agents administered with the DR5 targeting agent may be a DNA damage response inhibitor (DDRi). DNA damage can be due to endogenous factors, such as spontaneous or enzymatic reactions, chemical reactions, or errors in replication, or may be due to exogenous factors, such as UV or ionizing radiation or genotoxic chemicals. The repair pathways that overcome this damage are collectively referred to as the DNA damage response or DDR. This signaling network acts to detect and orchestrate a cell's response to certain forms of DNA damage, most notably double strand breaks and replication stress. Following treatment with many types of DNA damaging drugs and ionizing radiation, cells are reliant on the DDR for survival. It has been shown that disruption of the DDR can increase cancer cell sensitivity to these DNA damaging agents and thus may improve patient responses to such therapies.

TABLE 1

| DNA repair mechanism | Gene examples | Cancer |
|---|---|---|
| Base Excision | OGG1 | Renal, breast and lung cancer |
| Repair | XRCC1 | Non-small cell lung cancer |
| Nucleotide | ERCC1 | Lung and skin cancer, and glioma |
| Excision Repair | XP | Xeroderma pigmentosum predisposing to skin cancer. Also increased risk of bladder and lung cancer |
| Mismatch Repair | MSH2, MLH1 | Lynch syndrome predisposing to colorectal cancer as well as endometrial, ovarian, stomach, small intestine, hepatobiliary tract, upper urinary tract, brain and skin cancer |
| Homologous Recombinant Repair | BRCA1, BRCA2 | Increased risk of breast, ovarian, prostate, pancreatic, as well as gastrointestinal and hematological cancer, and melanoma |
| Non-homologous | KU70 | Breast, colorectal and lung cancer |
| End Joining | KU80 | Lung cancer |
| Cell cycle | ATM | Ataxia-telangiectasia predisposing to leukemia, breast and pancreatic cancer |
| checkpoints | ATR | Leukemia, lymphoma, gastric and endometrial cancer |

Within the DDR, there are several DNA repair mechanisms, including base excision repair, nucleotide excision repair, mismatch repair, homologous recombinant repair, and non-homologous end joining. Approximately 450 human DDR genes code for proteins with roles in physiological processes. Dysregulation of DDR leads to a variety of disorders, including genetic, neurodegenerative, immune, cardiovascular, and metabolic diseases or disorders and cancers. For example, the genes OGGI and XRCCI are part of the base excision repair mechanism of DDR, and mutations in these genes are found in renal, breast, and lung cancers, while the genes BRCA1 and BRCA2 are involved in homologous recombination repair mechanisms and mutations in these genes leads to an increased risk of breast, ovarian, prostate, pancreatic, as well as gastrointestinal and hematological cancers, and melanoma. Exemplary DDR genes are provided in Table 1.

The present disclosure provides methods of treatment that include administration of an ARC that deliver ionizing radiation in combination with a DDRi. Thus, according to certain aspects, the additional agent(s) administered with the ARC may target proteins in the DDR, i.e., DDR inhibitors or DDRi, thus maximizing DNA damage or inhibiting repair of the damage, such as in G1 and S-phase and/or preventing repair in G2, ensuring the maximum amount of DNA damage is taken into mitosis, leading to cell death.

Moreover, one or more DDR pathways may be targeted to ensure cell death, i.e., lethality to the targeted cancer cells. For example, mutations in the BRCA1 and 2 genes alone may not be sufficient to ensure cell death, as other pathways, such as the PARP1 base excision pathway, may act to repair the DNA damage. Thus, combinations of multiple DDRi inhibitors or combining DDRi with antiangiogenic agents or immune checkpoint inhibitors, such as listed hereinabove, are possible and an object of the present disclosure.

Exemplary DDRi—ATM and ATR Inhibitors

Ataxia telangiectasia mutated (ATM) and Ataxia talangiectasia mutated and Rad-3 related (ATR) are members of the phosphatidylinositol 3-kinase-related kinase (PIKK) family of serine/threonine protein kinases.

ATM is a serine/threonine protein kinase that is recruited and activated by DNA double-strand breaks. The ATM phosphorylates several key proteins that initiate activation of a DNA damage checkpoint, leading to cell cycle arrest, DNA repair, or cellular apoptosis. Several of these targets, including p53, CHK2, and H2AX, are tumor suppressors. The protein is named for the disorder ataxia telangiectasia caused by mutations of the ATM. The ATM belongs to the superfamily of phosphatidylinositol 3-kinase-related kinases (PIKKs), which includes six serine/threonine protein kinases that show a sequence similarity to a phosphatidylinositol 3-kinase (PI3K).

Like ATM, ATR is one of the central kinases involved in the DDR. ATR is activated by single stranded DNA structures, which may for example arise at resected DNA DSBs or stalled replication forks. When DNA polymerases stall during DNA replication, the replicative helicases continue to unwind the DNA ahead of the replication fork, leading to the generation of long stretches of single stranded DNA (ssDNA).

ATM has been found to assist cancer cells by providing resistance against chemotherapeutic agents and thus favors tumor growth and survival. Inhibition of ATM and/or ATR may markedly increase cancer cell sensitivity to DNA damaging agents, such as the ionizing radiation provided by the ARC (e.g., radiolabeled anti-DR5 antibodies). Accordingly, the present disclosure also provides administration of an inhibitor of ATM (ATMi) and/or ATR (ATRi), in combination with the ARC (e.g., radiolabeled anti-DR5 antibodies), to inhibit or kill cancer cells, such as those expressing or overexpressing DR5.

The inhibitor of ATM (ATMi) or ATR (ATRi) may be an antibody, peptide, or small molecule that targets ATM or ATR, respectively. Alternatively, an ATMi or ATRi may reduce or eliminate activation of ATM or ATR by one or more signaling molecules, proteins, or other compounds, or can result in the reduction or elimination of ATM or ATR activation by all signaling molecules, proteins, or other compounds. ATMi and/or ATRi also include compounds that inhibit their expression (e.g., compounds that inhibit ATM or ATR transcription or translation). An exemplary ATMi KU-55933 suppresses cell proliferation and induces apoptosis. Other exemplary ATMi include at least KU-59403, wortmannin, CP466722, and KU-60019. Exemplary ATRi include at least Schisandrin B, NU6027, NVP-BEA235, VE-821, VE-822, AZ20, and AZD6738.

Exemplary DDRi—Wee1 Inhibitors

The checkpoint kinase Wee1 catalyzes an inhibitory phosphorylation of both CDK1 (CDC2) and CDK2 on tyrosine 15, thus arresting the cell cycle in response to extrinsically induced DNA damage. Deregulated Wee1 expression or activity is believed to be a hallmark of pathology in several types of cancer. For example, Wee1 is often overexpressed in glioblastomas, malignant melanoma, hepatocellular carcinoma, breast cancer, colon carcinoma, lung carcinoma, and head and neck squamous cell carcinoma. Advanced tumors with an increased level of genomic instability may require functional checkpoints to allow for repair of such lethal DNA damage. As such, the present inventors believe that Wee1 represents an attractive target in advanced tumors where its inhibition is believed to result in irreparable DNA damage. Accordingly, the present disclosure also provides for administration of an inhibitor of Wee1, in combination with the ARC, to inhibit or kill cancer cells, such as those expressing or overexpressing DR5.

A Wee1 inhibitor may be an antibody, peptide, or small molecule that targets Wee1. Alternatively, a Wee1 inhibitor may reduce or eliminate Wee1 activation by one or more signaling molecules, proteins, or other compounds, or can result in the reduction or elimination of Wee1 activation by all signaling molecules, proteins, or other compounds. The term also includes compounds that decrease or eliminate the activation or deactivation of one or more proteins or cell signaling components by Wee1 (e.g., a Wee1 inhibitor can decrease or eliminate Wee1-dependent inactivation of cyclin and Cdk activity). Wee1 inhibitors also include compounds that inhibit Wee1 expression (e.g., compounds that inhibit Wee1 transcription or translation).

Exemplary Wee1 inhibitors include AZD-1775 (i.e., adavosertib), and inhibitors such as those described in, e.g., U.S. Pat. Nos. 7,834,019; 7,935,708; 8,288,396; 8,436,004; 8,710,065; 8,716,297; 8,791,125; 8,796,289; 9,051,327; 9,181,239; 9,714,244; 9,718,821; and 9,850,247; U.S. Pat. App. Pub. Nos. US 2010/0113445 and 2016/0222459; and Intl Pat. App. Pub. Nos. WO 2002/090360, 2015/019037, 2017/013436, 2017/216559, 2018/011569, and 2018/011570.

Further Wee1 inhibitors include a pyrazolopyrimidine derivative, a pyridopyrimidine, 4-(2-chlorophenyl)-9-hydroxypyrrolo[3,4-c]carbazole-1,3-(2H, 6H)-dione (CAS No. 622855-37-2), 6-butyl-4-(2-chlorophenyl)-9-hydroxypyrrolo[3,4-c]carbazole-1,3-(2H,6H)-dione (CAS No. 62285550-9), 4-(2-phenyl)-9-hydroxypyrrolo[3,4-c]carbazole-1,3-(2H,6H)-dione (CAS No. 1177150-89-8), and an anti-Wee1 small interfering RNA (siRNA) molecule.

Exemplary DDRi—PARP Inhibitors

Another exemplary DDRi of the presently disclosed invention is an inhibitor of poly(ADP-ribose) polymerase ("PARP"). Inhibitors of the DNA repair protein PARP, referred to individually and collectively as "PARPi", have been approved for use in a range of solid tumors, such as breast and ovarian cancer, particularly in patients having BRCA1/2 mutations.

To date, the FDA has approved four PARPi drugs (olaparib, niraparib, rucaparib and talazoparib) as monotherapy agents, specifically in patients with germline and somatic mutations in the BRCA1 and BRCA2 genes. Along with veliparib, olaparib, niraparib and rucaparib were among the first generation of PARPi that entered clinical trials. Their IC50 values were found to be in the nanomolar range. In contrast, second generation PARPi like talazoparib have IC50 values in the picomolar range.

These PARPi all bind to the binding site of the cofactor, b nicotinamide adenine dinucleotide (b-NAD+), in the catalytic domain of PARP1 and PARP2. The PARP family of enzymes use NAD+ to covalently add Poly(ADP-ribose) (PAR) chains onto target proteins, a process termed "PARylation." PARP1 (which is the best-studied member) and PARP2, are important components of the DNA damage response (DDR) pathway. PARP1 is involved in the repair of single-stranded DNA breaks, and possibly other DNA lesions (Woodhouse, et al.; Krishnakumar, et al.). Through its zinc finger domains, PARP1 binds to damaged DNA and then PARylates a series of DNA repair effector proteins, releasing nicotinamide as a by-product (Krishnakumar, et al.). Subsequently, PARP1 auto-PARylation leads to release of the protein from the DNA. The available PARPi, however, differ in their capability to trap PARP1 on DNA, which seems to correlate with cytotoxicity and drug efficacy. Specifically, drugs like talazoparib and olaparib are more effective in trapping PARP1 than are veliparib (Murai, et al., 2012; Murai, et al., 2014).

Clinically, therapy with PARPi has resulted in sustained anti-tumor responses in a range of cancers including ovarian, prostate, pancreatic, and triple-negative breast cancers (TNBC). In one clinical trial, TNBC patients with germline BRCA1/2 mutations were treated with the PARPi, olaparib. While this therapy demonstrated a higher disease stabilization rate in BRCA1/2-mutant compared to non-mutant patients, there were no sustained responses achieved in either cohort (Gelmon, 2011). Preclinical studies have demonstrated that combining radiation therapy and PARPi can increase the sensitivity of BRCA1/2 mutant tumor cells to PARP inhibition and extend the sensitivity of non-mutant BRCA tumors to PARP inhibition. Additional studies have shown that ionizing radiation (IR) itself can mediate PARPi synthetic lethality in tumor cells.

The present inventors realized that the effect of PARPi may be improved through increases in dsDNA breaks induced by ionizing radiation provided by an ARC while these repair pathways are being blocked by the PARPi. Exemplary PARPi include olaparib, niraparib, rucaparib and talazoparib.

Accordingly, the present disclosure further provides administration of an ARC that deliver ionizing radiation in combination with a PARPi. Exemplary PARPi may be any known agent performing that function, and preferably, one approved by the FDA. Preferably, the PARPi is olaparib (Lynparza®), niraparib (Zejula®), rucaparib (Rubraca®) or talazoparib (Talzenna®).

Methods of the Invention

The present invention includes methods for treating, ameliorating or reducing the severity of at least one symptom or indication, or inhibiting the growth of a cancer in a subject by administering a therapeutically effective amount of an ARC.

The present invention further includes methods for treating, ameliorating or reducing the severity of at least one symptom or indication, or inhibiting the growth of a cancer in a subject by administering a therapeutically effective amount of an ARC and a therapeutically effective amount of an immune checkpoint therapy, e.g., an ICI antibody, and/or a DDR inhibitor, i.e., DDRi, such as a PARPi.

The present invention further includes methods for initiating, enhancing, or prolonging an anti-tumor response in a subject by administering a therapeutically effective amount of an ARC and a therapeutically effective amount of an immune checkpoint therapy (e.g., ICI antibody) and/or a DDRi.

The present invention further includes methods for treating a proliferative disease or disorder in a subject by administering an ARC.

The present invention further includes methods for treating a proliferative disease or disorder in a subject by administering an ARC and a therapeutically effective amount of an immune checkpoint therapy and/or a DDRi.

According to certain aspects of the present invention, the methods may treat subjects with tumors having a standard or even high mutational burden, such as breast cancer, ovarian cancer, or prostate cancer.

According to certain aspects of the present invention, the methods may treat subjects with tumors having a standard or even high mutational burden, such as breast cancer, ovarian cancer, or prostate cancer, wherein the subjects are poor responders or non-responders to standard immunotherapies.

According to certain aspects, the methods may treat subjects with tumors that are known to be immunologically cold. That is, the ARC administered in the methods may target antigens from tumors having a low mutational burden.

According to certain aspects, the methods may treat subjects with tumors, wherein the subject does not possess a deleterious BRCA1/2 mutation, or wherein the subject does possess a deleterious BRCA1/2 mutation.

According to certain aspects, the ARC and the immune checkpoint therapy and/or DDRi may be administered simultaneously. As such, they may be provided as a single composition, or they may be provided as separate compositions administered simultaneously. The combination may be administered in a single dose, such as together or within the same day, such as within several minutes or hours of each other. Alternatively, the combination may be administered simultaneously as defined, but according to a dosing schedule selected from the group consisting of once every 1, 2, 3, 4, 5, 6, 7, 8, 9, 10, 12, 14, 20, 24, or 28 days throughout a treatment period, wherein the treatment period includes at least two doses.

According to certain aspects, the ARC and the immune checkpoint therapy and/or DDRi may be administered sequentially. Moreover, each therapy regime, i.e., ARC and immune checkpoint therapy, DDRi, or combination immune checkpoint therapy and DDRi, may be administered according to a specific dosing schedule, wherein the method provides for administration of each therapy according to the dosing schedule sequentially, i.e., the ARC dosing schedule is completed before the immune checkpoint therapy and/or DDRi dosing schedule is started, or vice versa.

For example, the ARC may be administered in one or more doses prior to administration of the immune checkpoint therapy and/or DDRi, or the immune checkpoint therapy and/or DDRi may be administered in one or more doses prior to administration of the ARC.

According to certain aspects, more than one ARC may be administered to a patient, wherein a first and second ARC may be administered simultaneously, or sequentially. The immune checkpoint therapy and/or DDRi may be administered before or after the first and second ARC or may be administered after the first ARC and before the second ARC.

According to certain aspects, the ARC and the immune checkpoint therapy and/or DDRi may be administered according to specific dosing schedules that are carried out simultaneously. That is, doses of the ARC may be administered during the administration schedule of the immune checkpoint therapy and/or DDRi, or vice versa. For example, doses of the ARC and the immune checkpoint therapy and/or DDRi may be given, wherein individual doses of each therapeutic agent are administered in overlapping dosing schedules.

According to certain aspects, the ARC may be administered in a single dose. Alternatively, the ARC may be administered according to a dosing schedule selected from the group consisting of once every 1, 2, 3, 4, 5, 6, 7, 8, 9, 10, 12, 14, 20, 24, or 28 days throughout a treatment period, wherein the treatment period includes at least two doses. The ARC may be administered during a weekly schedule, such as once every weekday but not on weekend days (Saturday or Sunday). Moreover, each dose may be the same, or may be different. For example, a first dose or set of doses of the ARC may be larger (induction doses) than additional doses or sets of doses (continuation doses).

According to certain aspects, the immune checkpoint therapy may be administered in a single dose. Alternatively, the immune checkpoint therapy may be administered according to a dosing schedule selected from the group consisting of once every 1, 2, 3, 4, 5, 6, 7, 8, 9, 10, 12, 14, 20, 24, or 28 days throughout a treatment period, wherein the treatment period includes at least two doses. The immune checkpoint therapy may be administered during a weekly schedule, such as once every weekday but not on weekend days (Saturday or Sunday). Moreover, each dose may be the same, or may be different. For example, a first dose or set of doses of the immune checkpoint therapy may be larger (induction dose(s)) than additional doses or sets of doses (continuation doses).

According to certain aspects, the DDRi may be administered in a single dose. Alternatively, the DDRi may be administered according to a dosing schedule selected from the group consisting of once every 1, 2, 3, 4, 5, 6, 7, 8, 9, 10, 12, 14, 20, 24, or 28 days throughout a treatment period, wherein the treatment period includes at least two doses. The DDRi may be administered during a weekly schedule, such as once every weekday but not on weekend days (Saturday or Sunday). Moreover, each dose may be the same, or may be different. For example, a first dose or set of doses of the DDRi may be larger (induction dose(s)) than additional doses or sets of doses (continuation doses).

According to certain aspects, the therapeutically effective amount of the ARC may comprise a radiation dose dependent on the selected radionuclide used for the labeling. For example, when a radionuclide such as $^{225}$Ac is selected for the ARC, the radiation dose may be about 0.1 to 20 uCi/kg patient body weight, such as 0.2 to 10 uCi/kg patient body weight, or 0.2 to 5 uCi/kg patient body weight, or 0.4 to 4 uCi/kg patient body weight, or 0.4 to 3 uCi/kg patient body weight, or even 0.4 to 2 uCi/kg patient body weight. When $^{131}$I is selected for the ARC, the radiation dose may be at least 10 mCi, such as at least 20 mCi, or 30 mCi, or 40 mCi, and may have an upper dose limit of no more than 400 mCi, such as no more than 300 mCi, or no more than 200 mCi. The dose of an $^{131}$I comprising ARC may be any combination of lower and upper radiation doses, such as from 10 mCi to 200 mCi.

The effective dose of the ARC generally comprises a protein dose of less than 16 mg/kg patient body weight, such as less than 10 mg/kg patient body weight, or less than 6 mg/kg patient body weight, or less than 5 mg/kg patient body weight, or less than 4 mg/kg patient body weight, or less than 3 mg/kg patient body weight, or even less than 2 mg/kg patient body weight. According to certain aspects, the protein dose may be from 0.05 mg/kg to 16 mg/kg body weight of the subject, such as 0.05 mg/kg to 10 mg/kg, or 0.05 mg/kg to 6 mg/kg, or 0.1 mg/kg to 4 mg/kg, or 0.1 mg/kg to 2 mg/kg, or 0.5 mg/kg to 16 mg/kg, or 2 mg/kg to 16 mg/kg, or 4 mg/kg to 16 mg/kg, or 6 mg/kg to 16 mg/kg.

According to certain aspects, the effective dose of the ARC may comprise a protein dose based on the patient's body surface area, such as a dose of less than 10 mg/m2, or 8 mg/m2, or 6 mg/m2, or 5 mg/m2, or 4 mg/m2, or 3 mg/m2, or 2 mg/m2, or 1 mg/m2, or 0.5 mg/m2. The protein dose useful in the methods of the present disclosure are at least 10× lower, such as 20× lower, or 50× lower, or even at least 100× lower than therapeutic doses for an unlabeled antibody (i.e., naked antibody).

According to certain aspects, the effective amount of the ARC may be a maximum tolerated dose (MTD) of the ARC, based on either or both of the protein dose and the radiation dose.

According to certain aspects, the ARC may comprise a mixture of a radiolabeled fraction of an antibody and an un-labeled (e.g., "naked") fraction of the antibody. The un-labeled fraction may comprise the same antibody against the same epitope as the labeled fraction. In this way, the total radioactivity of the ARC may be reduced or set while the overall antibody concentration may be varied. For example, the total protein concentration and the total radioactivity of the ARC may be independently varied based on the exact nature of the disease to be treated, age and weight of the patient, identity of the antibody, and the label (e.g., radionuclide) selected for labeling of the monoclonal antibody.

According to certain aspects, the immune checkpoint therapy may comprise an antibody against CTLA-4, PD-1, TIM-3, VISTA, BTLA, LAG-3, TIGIT, CD28, OX40, GITR, CD137, CD40, CD40L, CD27, HVEM, PD-L1, PD-L2, PD-L3, PD-L4, CD80, CD86, CD137-L, GITR-L, CD226, B7-H3, B7-H4, BTLA, TIGIT, GALS, KIR, 2B4, CD160, CGEN-15049, or a combination thereof.

According to certain aspects, the immune checkpoint therapy may comprise an antibody against an immune checkpoint inhibitor (ICI), such as an antibody against PD-1, PD-L1, PD-L2, CTLA-4, and a combination thereof. Exemplary doses for certain of ICI antibodies include individual doses of from 0.1 mg/kg to 50 mg/kg of the patient's body weight, such as 0.1-40 mg/kg, or 0.1-30 mg/kg, or 0.1-20 mg/kg, or 0.1-10 mg/kg, or 0.1-5 mg/kg, or 0.1-4 mg/kg, or 0.1-3 mg/kg, or 0.1-2 mg/kg, or 1-50 mg/kg, or 2-40 mg/kg, or 5-30 mg/kg, or 5-20 mg/kg, or 10-20 mg/kg, or 1-5 mg/kg, or 1-10 mg/kg. For example, dosing for pembrolizumab (anti-PD-1; Keytruda®) and nivolumab (anti-PD-1; Opdivo®) may be 1-5 mg/kg, such as 2 mg/kg or 3 mg/kg of the patient's body weight; and dosing for Durvalumab (anti-PD-L1; MEDI4736) may be 10 mg/kg to 20 mg/kg of the patient's body weight. Dosing for anti-CTLA-4 (Yervoy®) 1-15 mg/kg, such as 2 mg/kg or 3 mg/kg of the patient's body weight every three weeks for a maximum of 4 doses.

According to certain aspects, the DDRi may be a PARPi. Exemplary doses for certain PARPi include individual doses of from 0.1 mg/day to 1200 mg/day, such as 0.1-1 mg/day or 100-1200 mg/day, provided orally. For example, Talazoparib (Talzenna™; Pfizer Labs) may be provided as 0.1 mg/day, or 0.2 mg/day, or 0.3 mg/day, or 0.4 mg/day, or 0.5 mg/day, or 0.6 mg/day, or 0.7 mg/day, or 0.8 mg/day, or 0.9 mg/day, or 1 mg/day taken orally. Olaparib (Lynparza®; AstraZeneca) or Niraparib (Zejula®; Tesaro) or Rucaparib (Rubraca™, Clovis Oncology, Inc.) may be provided as 50 mg/day, or 100 mg/day, or 150 mg/day, or 200 mg/day, or 250 mg/day, or 300 mg/day, or 350 mg/day, or 400 mg/day, or 450 mg/day, or 500 mg/day, or 550 mg/day, or 600 mg/day, or 650 mg/day, or 700 mg/day, or 750 mg/day, or 800 mg/day, or 850 mg/day, or 900 mg/day, or 950 mg/day, or 1000 mg/day, or 1050 mg/day, or 1100 mg/day, or 1150 mg/day, or 1200 mg/day.

Additional Agents

The methods of the present invention, which include administration of an ARC and an immune checkpoint therapy and/or DDRi, may further comprise administering one or more additional therapeutic agents or modalities. The additional therapeutic agents or modalities may be relevant for the disease or condition to be treated. Such administration may be simultaneous, separate or sequential with the administration of the effective amount of the ARC and the immune checkpoint therapy and/or DDRi regimes detailed herein. For simultaneous administration, the agents may be administered as one composition, or as separate compositions, as appropriate.

Exemplary additional therapeutic agents include at least chemotherapeutic agents, anti-inflammatory agents, immunosuppressive agents, immunomodulatory agents, external beam radiation, or a combination thereof. Exemplary chemotherapeutic and anti-inflammatory agents are well known in the art and within the scope of the presently disclosed invention.

Chemotherapeutic Agents

Exemplary chemotherapeutic agents include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolomide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguamne, azathioprine, T-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with antibodies of the invention.

According to certain aspects of the present invention, the chemotherapeutic agents include at least radiosensitizers, such as temozolomide, cisplatin, and/or fluorouracil.

The therapeutic agents may be administered according to any standard dose regime known in the field. For example, therapeutic agents may be administered at concentrations in the range of 1 to 500 mg/m2, the amounts being calculated as a function of patient surface area ($m^2$). For example, exemplary doses of the chemotherapeutic paclitaxel may include 15 mg/m2 to 275 mg/m2, exemplary doses of docetaxel may include 60 mg/m2 to 100 mg/m2, exemplary doses of epithilone may include 10 mg/m2 to 20 mg/m2, and an exemplary dose of calicheamicin may include 1 mg/m2 to 10 mg/m2. While exemplary doses are listed herein, such are only provided for reference and are not intended to limit the dose ranges of the drug agents of the presently disclosed invention.

External Beam Radiation and/or Brachytherapy

The additional therapeutic modality administered with the ARC, and optionally any other of the additional therapeutics disclosed herein, may be an ionizing radiation, such as administered via external beam radiation or brachytherapy. Such radiation generally refers to the use of X-rays, gamma rays, or charged particles (e.g., protons or electrons) to generate ionizing radiation, such as delivered by a machine placed outside the patient's body (external-beam radiation therapy) or by a source placed inside a patient's body (internal radiation therapy or brachytherapy).

The external beam radiation or brachytherapy may enhance the targeted radiation damage delivered by the ARC and may thus be delivered sequentially with the ARC, such as before and/or after the ARC, or simultaneous with the ARC.

The external beam radiation or brachytherapy may be planned and administered in conjunction with imaging-based techniques such as computed tomography (CT) and/or magnetic resonance imaging (MRI) to accurately determine the dose and location of radiation to be administered. For example, a patient treated with any of the ARC disclosed herein may be imaged using either of CT or MRI to determine the dose and location of radiation to be administered by the external beam radiation or brachytherapy.

In various embodiments, the radiation therapy may be selected from the group consisting of total all-body radiation therapy, conventional external beam radiation therapy, stereotactic radiosurgery, stereotactic body radiation therapy, 3-D conformal radiation therapy, intensity-modulated radiation therapy, image-guided radiation therapy, tomotherapy, and brachytherapy. According to certain aspects, the radiation therapy may be provided as a single dose or as fractionated doses, e.g., as 2 or more fractions. For example, the dose may be administered such that each fraction comprises 2-20 Gy (e.g., a radiation dose of 50 Gy may be split up into 10 fractions, each comprising 5 Gy). The 2 or more fractions may be administered on consecutive or sequential days, such as once in 2 days, once in 3 days, once in 4 days, once in 5 days, once in 6 days, once in 7 days, or in a combination thereof.

ASPECTS OF THE INVENTION

The following aspects are disclosed in this application:

Aspect 1: A method for treating a subject having cancer, the method comprising: administering to the subject a therapeutically effective amount of an ARC.

Aspect 2: The method according to aspect 1, wherein the subject does not possess a deleterious BRCA1/2 mutation, or wherein the subject does possess a deleterious BRCA1/2 mutation.

Aspect 3: A method for treating a subject having a proliferative disorder, the method comprising: administering to the subject a therapeutically effective amount of an immune checkpoint therapy and/or a DDRi; and after at least one day, administering to the subject a therapeutically effec-tive amount of an ARC.

Aspect 4: A method for treating a subject having a proliferative disorder, the method comprising: administering to the subject a therapeutically effective amount of an ARC; and after at least one day, administering to the subject a therapeutically effective amount of an immune checkpoint therapy and/or a DDRi.

Aspect 5: A method for treating a subject having a proliferative disorder, the method comprising: administering to the subject a therapeutically effective amount of an ARC; and administering to the subject a therapeutically effective amount of an immune checkpoint therapy and/or a DDRi.

Aspect 6: The method according to any preceding aspect, wherein administration of the ARC and/or immune checkpoint therapy and/or DDRi is according to a dosing schedule selected from the group consisting of once every 1 day, 2 days, 3 days, 4 days, 5 days, 6 days, 7 days, 10 days, 14 days, 21 days, or 28 days, wherein the treatment period includes at least two doses.

Aspect 7: The method according to any preceding aspect, wherein the ARC comprises a radionuclide complexed by a chelating agent attached to the antibody of the ARC, where the chelating agent comprises 1,4,7,10-tetraazacyclododecane-1,4,7,10-tetraacetic acid (DOTA) or a derivative thereof.

Aspect 8. The method according to any preceding aspect, wherein the ARC comprises a radionuclide selected from the group comprising $^{225}$Ac, $^{213}$Bi, $^{227}$Th, $^{212}$Pb, $^{211}$ At, $^{177}$Lu, $^{90}$Y, $^{131}$I, $^{67}$Cu, or a combination thereof.

Aspect 9. The method according to any preceding aspect, wherein the ARC comprises an antibody against DR5.

Aspect 10. The method according to any preceding aspect, wherein the ARC comprises a $^{225}$ Ac-anti-DR5 antibody, and the therapeutically effective amount of the ARC comprises a radiation dose of 0.1 to 10 uCi/kg body weight of the subject; or 0.2 to 6 uCi/kg body weight of the subject; or 0.4 to 5 uCi/kg body weight of the subject.

Aspect 11. The method according to any preceding aspect, wherein the ARC comprises an $^{177}$Lu-anti-DR5 antibody, and the therapeutically effective amount of the ARC comprises a radiation dose of 10 mCi to 1000 mCi, such as at least 20 mCi, or at least 30 mCi, or at least 40 mCi, or at least 50 mCi, and may have an upper limit if no more than 1000 mCi, such as no more than 900 mCi, 800 mCi, 700 mCi, 600 mCi, 500 mCi, 400 mCi, 300 mCi, 200 mCi, or any combination of the doses listed, such as from 10 mCi to 200 mCi.

Aspect 12. The method according to any preceding aspect, wherein the ARC comprises an $^{131}$I-anti-DR5 antibody, and the therapeutically effective amount of the ARC comprises a radiation dose of 10 mCi to 1000 mCi, such as at least 20 mCi, or at least 30 mCi, or at least 40 mCi, or at least 50 mCi, and may have an upper limit if no more than 1000 mCi, such as no more than 900 mCi, 800 mCi, 700 mCi, 600 mCi, 500 mCi, 400 mCi, 300 mCi, 200 mCi, or any combination of the doses listed, such as from 10 mCi to 200 mCi.

Aspect 13. The method according to any preceding aspect, wherein the cancer or proliferative disorder is a solid cancer.

Aspect 14. The method according to any preceding aspect, wherein the cancer or proliferative disorder is breast cancer, ovarian cancer, prostate cancer, lung cancer, squamous cell carcinoma of the head and neck, gastric cancer, pancreatic cancer, brain cancer (e.g., glioblastoma and neuroblastoma), liver cancer, sarcoma and melanoma.

Aspect 15. The method according to any preceding aspect, wherein the solid cancer is breast cancer, triple negative breast cancer, ovarian cancer, or prostate cancer.

Aspect 16. The method according to any preceding aspect, wherein the therapeutically effective amount of the ARC comprises a protein dose of less than 16 mg/kg body weight of the subject; or less than 10 mg/kg body weight of the subject; or less than 6 mg/kg body weight of the subject; or from 0.1 mg/kg to 16 mg/kg body weight of the subject.

Aspect 17. The method according to any preceding aspect, wherein the therapeutically effective amount of the ARC comprises a single dose that delivers less than 2Gy, or less than 8 Gy, such as doses of 2 Gy to 8 Gy, to the subject.

Aspect 18. The method according to any preceding aspect, wherein the immune checkpoint therapy may comprise an antibody against CTLA-4, PD-1, TIM-3, VISTA, BTLA, LAG-3, TIGIT, CD28, OX40, GITR, CD137, CD40, CD40L, CD27, HVEM, PD-L1, PD-L2, PD-L3, PD-L4, CD80, CD86, CD137-L, GITR-L, CD226, B7-H3, B7-H4, BTLA, TIGIT, GALS, KIR, 2B4, CD160, CGEN-15049, or a combination thereof.

Aspect 19. The method according to any preceding aspect, wherein the immune checkpoint therapy may comprise an antibody against an immune checkpoint inhibitor (ICI), such as an ICI antibody selected from the group consisting of an antibody against PD-1, PD-L1, PD-L2, CTLA-4, and a combination thereof.

Aspect 20. The method according to any preceding aspect, wherein the DDRi comprises a poly(ADP-ribose) polymerase inhibitor (PARPi), an ataxia telangiectasia mutated inhibitor (ATMi), an ataxia talangiectasia mutated and Rad-3 related inhibitor (ATRi), or a Wee1 inhibitor.

Aspect 21. The method according to any preceding aspect, wherein the DDRi is a PARPi selected from the group consisting of olaparib, niraparib, rucaparib and talazoparib.

EXAMPLES

Example 1: Radiolabeling of MD5-1 with $^{111}$In and $^{225}$Ac

The conditions to radiolabel MD5-1 (Catalog #16-5883-82 from ThermoFisher Scientific) will first be established using Indium-111 ($^{111}$In) as a surrogate for $^{225}$Ac due to the similar radiochemical properties of the two isotopes (Banerjee, et al.), ease of handling of $^{111}$In, and cost/availability of the radioisotopes. The antibody is first conjugated to the dodecane tetraacetic acid (DOTA) linker, with the goal of achieving a DOTA-antibody ratio of 3-5. Chelation with $^{111}$In will then be performed and efficiency and purity of the resulting $^{111}$In-labeled MD5-1 antibody will be determined by HPLC and iTLC. Preliminary radiolabeling of MD5-1 with $^{111}$In has been performed by Invicro and resulted in a labeling efficiency of >99%, specific activity of 10.2 uCi/ug, and >99% radiochemical purity. The radiolabeling was performed twice, with near identical results. With initial radiolabeling conditions established using $^{111}$In, radiolabeling of MD5-1 with $^{225}$Ac was then attempted and resulted in a specific activity of 59 uCi/ug, and 84% radiochemical purity. A immunoreactive fraction (IRF) bead assay, as described by Sharma, et al., was performed without optimization for both $^{111}$In-DOTA-MD5-1 and $^{225}$Ac-DOTA-MD5-1 and resulted in 54% and 58% immunoreactivity, respectively. These results demonstrate the radiolabeling MD5-1 with $^{111}$In and $^{225}$Ac is feasible and achievable.

Example 2: Biodistribution of $^{111}$In-MD5-1 and Calculation of Absorbed Tumor Dose Biodistribution studies will be performed in mice with 4T1 tumors to establish the normal tissue distribution and dosimetry profile of the DR5-targeting ARC and to confirm the selective uptake of the radiolabeled MD5-1 antibody to the tumor. $^{111}$In will again be used as a surrogate for $^{225}$Ac due to the similar radiochemical properties of the two isotopes, and the increased sensitivity and reliability of detection of $^{111}$In-radiolabeled agents in vivo due to the gamma-emission from this isotope that does not occur with $^{225}$Ac (Banerjee, et al.; Borchardt, et al.). Five groups of 4 female mice (ages 6-8 weeks) each will be injected with $^{111}$In-labeled MD5-1 and one group of mice will be euthanized at each of the following time points: 4, 24, 48, 96, and 168 hours. Organs (liver, lung, kidney, spleen, brain, stomach, muscle, and tumor) will be harvested and gamma counts measured. These measurements will be used for dosimetry calculations in which the absorbed dose of radiation to each organ is determined, including the dose delivered to the tumor.

Example 3: Determine MTD and Single Agent Activity of $^{225}$Ac-MD5-1

Six (6) groups with 6 mice per group, with established subcutaneous 4T1 tumors (~150-200 mm3) will be injected with unlabeled MD5-1 (500 ng) or a dose escalation of $^{225}$Ac-MD5-1 (50, 100, 200, 400, 500 nanoCurie (nCi), 500 ng total antibody) to identify the maximum tolerated dose (MTD), which is defined as the highest administered activity that allows survival of all treated mice without resulting in >20% weight loss. Bodyweights and tumor measurements will be taken twice weekly for the 6-week duration of the study, beginning at animal arrival to the Invicro facility. Serum chemistry (Alanine Aminotransferase, Alkaline Phosphatase, Total bilirubin, Blood Urea Nitrogen, Calcium, Phosphorus, Total Protein, Albumin, Globulin, Albumin/Globulin Ratio, Amylase, Glucose, Total Cholesterol, Lipase) and complete blood counts (CBC) will be evaluated in animals on-study at baseline, week 3, and at the terminal time point. Humane euthanasia criteria include a decrease in body weight of >20%, or an increase in body weight due to ascites of >10%. Any signs of pain or distress will also be considered.

Animal health measurements and observations will be used to determine the MTD. Observations on tumor volume and survival will be noted and, combined with the toxicity/tolerability profile, will be used to determine the MTD of $^{225}$Ac-MD5-1. During this proof of concept stage, preliminary anti-tumor efficacy will be determined by tumor measurements, and survival will be used as a proxy for lung metastases, as has been previously reported (Demaria, et al.).

Example 4: Combination ARC and Immune Checkpoint Therapy

A 4T1 syngeneic mouse model was used, a common TNBC tumor model that does not express ER, PR, or Her2

(Kaur, et al.), thus making it a suitable TNBC model. 4T1 cells implanted subcutaneously in female Balb/c mice develop into aggressive tumors, with lung metastases developing 1-2 weeks post-implantation. As a result, even when the primary tumor is surgically resected or successfully ablated, mice still succumb in ~3 weeks due lung metastases (Oei, et al.; Uno, et al.).

Importantly, there is clear evidence that 4T1 tumors are responsive to DR5-targeted therapies, radiation, and immune checkpoint therapies such as an antibody against an ICI, individually and in combination. 4T1 cells express high levels of DR5 (Takeda, et al. (2004)), which has been confirmed by the present inventors in a flow cytometry study that detected high levels of DR5 on 4T1 with the anti-mouse DR5 antibody MD5-1 (FIG. 1). Takeda, et al., (2004) generated the MD5-1 and evaluated its activity as a single agent therapeutic in the 4T1 model (Takeda, et al. (2004)). This study demonstrated that for 4T1 tumored mice, MD5-1 treatment was well-tolerated, specifically targeted DR5, and resulted in anti-tumor effects including inducing T cell mediated tumor killing. However, the ability of MD5-1 to mediate durable responses and efficacy against lung metastases as a single agent appears to be limited. Follow-up publications from this group used MD5-1 in combination with anti-CD40 and anti-CD137 ICI antibodies (Uno, et al.), or with an anti-CTLA-4 antibody added to this ICI combination therapy (Takeda, et al. (2010)) to treat the 4T1 mice. These combinations resulted in improved tumor control and survival (Uno, et al.; Takeda, et al. (2010)), yet a cocktail of four antibodies is a challenging strategy to pursue from a clinical development, regulatory, and safety perspective.

Additional papers establish that a radiation and an immune checkpoint therapy combination can improve control of primary and metastatic tumors and survival in the 4T1 model. Demaria et al. demonstrated that 12 gray units (Gy) of external beam radiation combined with an anti-CTLA-4 antibody resulted in better tumor control than single agent treatment, and that 2×12Gy combined with the anti-CTLA-4 induced one CR (of 7 mice) in this very aggressive tumor model (Demaria, et al.). The study concluded that the anti-tumor activity was due to induction of a cell-mediated memory response, as CD8+ depletion abrogated the therapeutic benefits of the treatment, and the mouse that achieved CR rejected re-implanted tumor cells upon rechallenge.

Additionally, Rodriguez-Ruiz showed that 3×8Gy of external radiation delivered to a primary 4T1 tumor, but not to a secondary tumor, in combination with anti-PD-1 and anti-CD137 ICI antibodies, resulted in improved control of the primary tumor, modest effects on the secondary tumor, and a more robust reduction in lung metastases compared to single agent treatments (Rodriguez-Ruiz, et al.). Finally, Oei, et al., similarly showed improved tumor control, survival, and reduced lung metastases in the 4T1 model when fractionated radiation therapy (3×8Gy) was used with ICI antibodies (anti-PD-1 and anti-CTLA-4). Together, these studies provide significant supporting evidence that 4T1 is an appropriate model to evaluate the effect of an anti-DR5 $^{225}$Ac-ARC in combination with an immune checkpoint therapy for the control of TNBC.

Example 5: Evaluate the Effect of Combination of Single Dose Versus Fractionated Dose of $^{225}$Ac-MD5-1 with Immune Checkpoint Inhibitor Antibody Two variables will be explored in a single experiment:

(A) Combination of $^{225}$Ac-MD5-1 ARC with an anti-PD-L1 antibody: Because the only ICI antibody currently approved for TNBC is an anti-PD-L1 antibody, an anti-mouse PD-L1 antibody (10F.9G2) will be used in this experiment. This anti-PD-L1 antibody has been tested in the 4T1 model and did not convey any tumor control benefit to treated mice (Grasselly, et al.), further establishing that 4T1 is an informative model to examine the ability of an ARC to improve response rates to immune checkpoint therapy in metastatic TNBC. Therefore, combining with an ARC provides the opportunity to sensitize the 4T1 tumors to this ICI antibody and determine if targeted radiation to the tumor can induce a systemic response that will treat both primary and metastatic tumors. Concurrent administration of radiation and the ICI antibody (3 doses, on alternating days) will be employed, as was determined by two groups that concurrent administration of an ARC in combination with 3 doses of an ICI antibody resulted in superior anti-tumor effects compared to sequential treatment (Chen, et al.; Jiao, et al.).

(B) Single vs fractionated dosing of $^{225}$Ac-MD5-1 in combination with an immune checkpoint therapy: For all three reports of the combination of radiation and immune checkpoint therapy in mice with 4T1 tumors, radiation was administered in multiple fractions (Demaria, et al.; Oei, et al.; Rodriguez-Ruiz, et al.). Rodriguez-Ruiz, et al., and Oei, et al., used a dosing regimen of 3×8Gy in combination with immune checkpoint therapy. Only Demaria, et al., directly compared a single dose (12 Gy) and multiple dosing (2×12Gy), with superior results obtained from the 2×12Gy treatment in the 4T1 model. There is further evidence in other models that fractionated external radiation may lead to superior outcomes compared to a single high dose of radiation in combination with immune checkpoint therapy. This was established in the TSA breast cancer model and the colon cancer model MC-38, and it was found that fractionated radiation (3×8Gy), but not a single high dose of 30Gy, in combination with a CTLA-4 antibody resulted in clearance of both a primary tumor (exposed to radiation) and a secondary tumor (not exposed to radiation; Vanpoulli-Box, et al.). This suggests that this combination regimen led to an abscopal response, where irradiation of one tumor leads to a systemic response and clearance of distal tumors that were not exposed to radiation, a phenomenon that has been reported in melanoma in combination with immune checkpoint therapy (Garelli, et al.). While the effect of radiation delivered by an ARC on a primary and secondary tumor cannot be measured independently due to the systemic nature of ARCs, the effect of high single dose vs low fractionated doses can still be explored. The metastatic nature and subsequent lethality of 4T1 tumors will allow investigation into the superior dosing strategy of ARC for survival.

TABLE 2

| Group | Test article | ARC Dosing | Anti-DR5 mAB | Anti-PD-L1 |
|---|---|---|---|---|
| 1 | Saline | Single | — | — |
| 2 | Anti-PD-L1 | N/A | — | D1, D3, D5 |
| 3 | DOTA-MD5-1 | Single MTD | D0 | — |
| 4 | $^{225}$Ac-DOTA-MD5-1 | Single MTD | D0 | — |
| 5 | $^{225}$Ac-DOTA-MD5-1 + Anti-PD-L1 | Single MTD | D0 | D1, D3, D5 |

TABLE 2-continued

| Group | Test article | ARC Dosing | Anti-DR5 mAB | Anti-PD-L1 |
|---|---|---|---|---|
| 6 | DOTA-MD5-1 | Fractionated (x3) | D0, D2, D4 | — |
| 7 | $^{225}$Ac-DOTA-MD5-1 | Fractionated (x3) | D0, D2, D4 | — |
| 8 | $^{225}$Ac-DOTA-MD5-1 + Anti-PD-L1 | Fractionated (x3) | D0, D2, D4 | D1, D3, D5 |

Mice will be randomized and treated starting when tumors have reached 150-200 mm$^3$, designated as Day 0 (DO), according to groups and schedule in Table 2. Each group will include 10 Balb/c mice, and all injections intraperitoneal. Each $^{225}$ Ac-MD5-1 treatment will be administered as total mass of 500 ng and each anti-PD-L1 treatment 200 μg. A control group will receive a single dose of DOTA-labelled, unchelated antibody (Group 3), and multiple doses (Group 6) (DOTA-MD5-1). Each fractionated dosing of $^{225}$ Ac-MD5-1 will be ⅓ of the MTD, thereby delivering the same total amount of radiation as the MTD. The Fractionated combination group (Group 8) will receive alternating doses of the $^{225}$ Ac-MD5-1 ARC and the ICI antibody, to mimic the administration of external beam radiation and immune checkpoint therapy combination reported by other groups (Oei, et al.; Rodriguez-Ruiz, et al.). Tumor size and bodyweights will be measured twice weekly for 6 weeks. Survival will be used as a proxy for lung metastases (Demaria, et al.). Mice that achieve a CR (complete resolution of primary tumor and survival through the 6-week study) will be observed for 4 additional weeks, then rechallenged with 4T1 cells to investigate if a memory response has been generated and will be followed for 6 additional weeks.

Example 6—Exemplary PARPi Administration and Dosing Regimes (A) Olaparib (Lynparza®)—Normal and Reduced Dosing Regimens Olaparib is sold by AstraZeneca under the brand name Lynparza®. Lynparza® is sold in tablet form at 100 mg and 150 mg. The dosage is 300 mg taken orally twice daily for a daily total of 600 mg. Dosing continues until disease progression or unacceptable toxicity. This dosing regimen is referred to herein as the "normal" human dosing regimen for Lynparza®, regardless of the disorder treated. Any dosing regimen having a shorter duration (e.g., 21 days) or involving the administration of less Lynparza® (e.g., 300 mg/day) is referred to herein as a "reduced" human dosing regimen. Examples of reduced human dosing regimens include the following: (i) 550 mg/day; (ii) 500 mg/day; (iii) 450 mg/day; (iv) 400 mg/day; (v) 350 mg/day; (vi) 300 mg/day; (vii) 250 mg/day; (viii) 200 mg/day; (ix) 150 mg/day; (x) 100 mg/day; or (xi) 50 mg/day.

(B) Niraparib (ZejulaR)—Normal and Reduced Dosing Regimens

Niraparib is sold by Tesaro under the brand name Zejula®. Zejula® is sold in capsule form at 100 mg. The dosage is 300 mg taken orally once daily. Dosing continues until disease progression or unacceptable adverse reaction. This dosing regimen is referred to herein as the "normal" human dosing regimen for Zejula®, regardless of the disorder treated. Any dosing regimen having a shorter duration (e.g., 21 days) or involving the administration of less Zejula® (e.g., 150 mg/day) is referred to herein as a "reduced" human dosing regimen. Examples of reduced human dosing regimens include the following: (i) 250 mg/day; (ii) 200 mg/day; (iii) 150 mg/day; (iv) 100 mg/day; or (v) 50 mg/day.

(C) Example 7—Rucaparib (Rubraca®)—Normal and Reduced Dosing Regimens

Rucaparib is sold by Clovis Oncology, Inc. under the brand name Rubraca™. Rubraca™ is sold in tablet form at 200 mg and 300 mg. The dosage is 600 mg taken orally twice daily for a daily total of 1,200 mg. Dosing continues until disease progression or unacceptable toxicity. This dosing regimen is referred to herein as the "normal" human dosing regimen for Rubraca™, regardless of the disorder treated. Any dosing regimen having a shorter duration (e.g., 21 days) or involving the administration of less Rubraca™ (e.g., 600 mg/day) is referred to herein as a "reduced" human dosing regimen. Examples of reduced human dosing regimens include the following: (i) 1,150 mg/day; (ii) 1,100 mg/day; (iii) 1,050 mg/day; (iv) 1,000 mg/day; (v) 950 mg/day; (vi) 900 mg/day; (vii) 850 mg/day; (viii) 800 mg/day; (ix) 750 mg/day; (x) 700 mg/day; (xi) 650 mg/day; (xii) 600 mg/day; (xiii) 550 mg/day; (xiv) 500 mg/day; (xv) 450 mg/day; (xvi) 400 mg/day; (xvii) 350 mg/day; (xviii) 300 mg/day; (xix) 250 mg/day; (xx) 200 mg/day; (xxi) 150 mg/day; or (xxii) 100 mg/day.

(D)—Talazoparib (Talzenna™)—Normal and Reduced Dosing Regimens

Talazoparib is sold by Pfizer Labs under the brand name Talzenna™. Talzenna™ is sold in capsule form at 1 mg. The dosage is 1 mg taken orally. Dosing continues until disease progression or unacceptable toxicity. This dosing regimen is referred to herein as the "normal" human dosing regimen for Talzenna™, regardless of the disorder treated. Any dosing regimen having a shorter duration (e.g., 21 days) or involving the administration of less Talzenna™ (e.g., 0.5 mg/day) is referred to herein as a "reduced" human dosing regimen. Examples of reduced human dosing regimens include the following: (i) 0.9 mg/day; (ii) 0.8 mg/day; (iii) 0.7 mg/day; (iv) 0.6 mg/day; (v) 0.5 mg/day; (vi) 0.4 mg/day; (vii) 0.3 mg/day; (viii) 0.2 mg/day; or (ix) 0.1 mg/day.

Example 7: Dosing Regimens for ARC and PARPi

A human patient may be treated according to the following regimen. One of olaparib, niraparib, rucaparib or talazoparib (PARPi) is orally administered according to one of the dosing regimens listed in Example 6, accompanied by intravenous administration of $^{225}$ Ac-DR5 as detailed herein in either single or fractional administration. For example, the dosing regimens include, by way of example: (a) the PARPi and ARC are administered concurrently, wherein (i) each is administered beginning on the same day, (ii) the ARC is administered in a single dose or fractionated doses not less than one week apart, and (iii) the PARPi is administered daily or twice daily (as appropriate), and for a duration equal to or exceeding that of the ARC administration; or (b) the PARPi and ARC are administered concurrently, wherein (i) the PARPi administration precedes ARC administration by at least one week, (ii) the ARC is administered in a single dose or fractionated doses not less than one week apart, and (iii) the PARPi is administered daily or twice daily (as appropriate), and for a duration equal to or exceeding that of the ARC administration.

REFERENCES

Atallah, E. L. et al. A Phase 2 Study of Actinium-225 ($^{225}$Ac)-Lintuzumab in Older Patients with Untreated Acute Myeloid Leukemia (AML)—Interim Analysis of 1.5 μci/Kg/Dose. *Blood* 132, 1457-1457 (2018).

Banerjee, S. R. et al. Evaluation of $^{111}$In-DOTA-5D3, a Surrogate SPECT Imaging Agent for Radioimmunotherapy of Prostate-Specific Membrane Antigen. *J. Nucl. Med.* 60, 400-406 (2019).

Bavi, P. et al. Prognostic significance of TRAIL death receptors in Middle Eastern colorectal carcinomas and their correlation to oncogenic KRAS alterations. *Mol. Cancer* 9, (2010).

Borchardt, P. E., Yuan, R. R., Miederer, M., McDevitt, M. R. & Scheinberg, D. A. Targeted Actinium-225 in Vivo Generators for Therapy of Ovarian Cancer. *Cancer Res.* 63, 5084-5090 (2003).

Chen, H. et al. Integrin α v β 3-targeted radionuclide therapy combined with immune checkpoint blockade immunotherapy synergistically enhances anti-tumor efficacy. *Theranostics* 9, 7948-7960 (2019).

Demaria, S. et al. Immune-mediated inhibition of metastases after treatment with local radiation and CTLA-4 blockade in a mouse model of breast cancer. *Clin. Cancer Res.* 11, 728-34 (2005).

Forero-Torres, A. et al. TBCRC 019: A Phase II Trial of Nanoparticle Albumin-Bound Paclitaxel with or without the Anti-Death Receptor 5 Monoclonal Antibody Tigatuzumab in Patients with Triple-Negative Breast Cancer. *Clin. Cancer Res.* 21, 2722-9 (2015).

Ganten, T. M. et al. Prognostic significance of tumour necrosis factor-related apoptosis-inducing ligand (TRAIL) receptor expression in patients with breast cancer. *J. Mol. Med.* 87, 995-1007 (2009).

Garelli, E. et al. Abscopal effect in lung cancer: three case reports and a concise review. *Immunotherapy* 11, 1445-1461 (2019).

Gelmon, et al., Olaparib in Patients With Recurrent High-Grade Serous or Poorly Differentiated Ovarian Carcinoma or Triple-Negative Breast Cancer: A Phase 2, *Multicentre*, Open-Label, Non-Randomized Study. *Lancet Oncol.* 12:852-61 (2011).

Grasselly, C. et al. The Antitumor Activity of Combinations of Cytotoxic Chemotherapy and Immune Checkpoint Inhibitors Is Model-Dependent. *Front. Immunol.* 9, 1-13 (2018).

Hiniker, S. M. et al. A Prospective Clinical Trial Combining Radiation Therapy With Systemic Immunotherapy in Metastatic Melanoma. *Int. J. Radiat. Oncol. Biol. Phys.* 96, 578-88 (2016).

Jiao, R., Allen, K. J. H., Malo, M. E., Rickles, D. & Dadachova, E. Evaluating the Combination of Radioimmunotherapy and Immunotherapy in a Melanoma Mouse Model. *Int. J. Mol. Sci.* 21, 773 (2020).

Jutzy, J. M. S., Lemons, J. M., Luke, J. J. & Chmura, S. J. The Evolution of Radiation Therapy in Metastatic Breast Cancer: From Local Therapy to Systemic Agent. *Int. J. Breast Cancer* 2018, 1-7 (2018).

Kaur, P. et al. A mouse model for triple-negative breast cancer tumor-initiating cells (TNBC-TICs) exhibits similar aggressive phenotype to the human disease. *BMC Cancer* 12, 120 (2012).

Krishnakumar and Kraus, The PARP Side of the Nucleus: Molecular Actions, Physiological Outcomes, and Clinical Targets. *Mol. Cell* 39 (1) 8-24 (2010).

Lamichhane, P., Amin, N., Agarwal, M. & Lamichhane, N. Checkpoint Inhibition: Will Combination with Radiotherapy and Nanoparticle-Mediated Delivery Improve Efficacy? *Medicines* 5, 114 (2018).

Macher-Goeppinger, S. et al. Prognostic value of tumor necrosis factor-related apoptosis-inducing ligand (TRAIL) and TRAIL receptors in renal cell cancer. *Clin. Cancer Res.* 15, 650-659 (2009).

Min, Y. J. et al. Prognostic significance of Fas (CD95) and TRAIL receptors (DR4/DR5) expression in acute myelogenous leukemia. *Leuk. Res.* 28, 359-365 (2004).

Mortland, L. et al. Clinical Significance of CD33 Nonsynonymous Single-Nucleotide Polymorphisms in Pediatric Patients with Acute Myeloid Leukemia Treated with Gemtuzumab-Ozogamicin-Containing Chemotherapy. *Clin. Cancer Res.* 19, 1620-1627 (2013).

Murai, J., et al., Trapping of PARP1 and PARP2 by Clinical PARP Inhibitors. *Cancer Res.* 72, 5588-5599 (2012).

Murai, J., et al., Stereospecific PARP Trapping by BMN 673 and Comparison with Olaparib and Rucaparib. *Mol Cancer Ther.* 13 (2), 433-443 (2014).

Naoum, G. E., Buchsbaum, D. J., Tawadros, F., Farooqi, A. & Arafat, W. O. Journey of TRAIL from Bench to Bedside and its Potential Role in Immuno-Oncology. *Oncol. Rev.* 11, 332 (2017).

Oei, A. L. et al. Enhancing the abscopal effect of radiation and immune checkpoint inhibitor therapies with magnetic nanoparticle hyperthermia in a model of metastatic breast cancer. *Int. J. Hyperth.* 36, 47-63 (2019).

Pedersen, M. H. et al. Downregulation of antigen presentation-associated pathway proteins is linked to poor outcome in triple-negative breast cancer patient tumors. *Oncoimmunology* 6, e1305531 (2017).

Pouget, J. P. et al. Clinical radioimmunotherapy—the role of radiobiology. *Nat. Rev. Clin. Oncol.* 8, 720-734 (2011).

Reits, E. A. et al. Radiation modulates the peptide repertoire, enhances MHC class I expression, and induces successful antitumor immunotherapy. *J. Exp. Med.* 203, 1259-1271 (2006).

Rodriguez-Ruiz, M. E. et al. Abscopal Effects of Radiotherapy Are Enhanced by Combined Immunostimulatory mAbs and Are Dependent on CD8 T Cells and Crosspriming. *Cancer Res.* 76, 5994-6005 (2016).

Schmid, P. et al. Atezolizumab and Nab-Paclitaxel in Advanced Triple-Negative Breast Cancer. *N. Engl. J. Med.* 379, 2108-2121 (2018).

Sharabi, A. B., Lim, M., DeWeese, T. L. & Drake, C. G. Radiation and checkpoint blockade immunotherapy: radiosensitisation and potential mechanisms of synergy. *Lancet. Oncol.* 16, e498-509 (2015).

Sharma, S. K. et al. A rapid bead-based radioligand binding assay for the determination of target-binding fraction and quality control of radiopharmaceuticals. *Nucl. Med. Biol.* 71, 32-38 (2019).

Song, H. et al. Radioimmunotherapy of Breast Cancer Metastases with Alpha-Particle Emitter $^{225}$Ac: Comparing Efficacy with $^{213}$Bi and $^{90}$Y. *Cancer Res.* 69, 8941-8948 (2009).

Spierings, D. C. et al. Tissue distribution of the death ligand TRAIL and its receptors. *J. Histochem. Cytochem.* 52, 821-31 (2004).

Takeda, K. et al. Combination Therapy of Established Tumors by Antibodies Targeting Immune Activating and Suppressing Molecules. *J. Immunol.* 184, 5493-5501 (2010).

Takeda, K. et al. Induction of Tumor-specific T Cell Immunity by Anti-DR5 Antibody Therapy. *J. Exp. Med.* 199, 437-448 (2004).

Tutt, et al., Oral poly(ADP-ribose) Polymerase Inhibitor Olaparib in Patients With BRCA1 or BRCA2 Mutations and Advanced Breast Cancer: A Proof-Of-Concept Trial. *Lancet.* 376:235-244 (2010).

Twyman-Saint Victor, C. et al. Radiation and dual checkpoint blockade activate non-redundant immune mechanisms in cancer. *Nature* 520, 373-377 (2015).

Uno, T. et al. Eradication of established tumors in mice by a combination antibody-based therapy. *Nat. Med.* 12, 693-698 (2006).

Vanpouille-Box, C. et al. DNA exonuclease Trex1 regulates radiotherapy-induced tumour immunogenicity. *Nat. Commun.* 8, 15618 (2017).

Wilson, N. S. et al. An Fcγ receptor-dependent mechanism drives antibody-mediated target-receptor signaling in cancer cells. *Cancer Cell* 19, 101-113 (2011).

Woodhouse B C, Dianova II, Parsons J L, Dianov G L. Poly(ADP-ribose) polymerase-1 modulates DNA repair capacity and prevents formation of DNA double strand breaks. DNA Repair (Amst) 7:932-940 (2008).

Xu, L. et al. Combinatorial surrobody libraries. *Proc. Natl. Acad. Sci. USA.* 105, 10756-10761 (2008).

Zhang, B. et al. Mislocalization of death receptors correlates with cellular resistance to their cognate ligands in human breast cancer cells. *Oncotarget* 3, (2012).

Zhang, L. & Fang, B. Mechanisms of resistance to TRAIL-induced apoptosis in cancer. *Cancer Gene Ther.* 12, 228-237 (2005).

What is claimed is:

1. A method for treating a cancer in a human subject, the method comprising:

administering to the subject a therapeutically effective amount of either or both of: (i) an immune checkpoint therapy selected from the group consisting of an antibody against PD-1, PD-L1, PD-L2, CTLA-4, or a combination thereof, and or (ii) a DNA damage response inhibitor (DDRi) comprising olaparib, niraparib, rucaparib, or talazoparib; and administering to the subject a therapeutically effective amount of a radiolabeled antibody against DR5, wherein the radiolabel comprises $^{225}$Ac, $^{213}$Bi, $^{227}$Th, $^{212}$Pb, $^{211}$At, $^{177}$Lu, $^{90}$Y, $^{131}$I, or $^{67}$Cu, wherein administering the therapeutically effective amount of the radiolabeled antibody against DR5 is performed at least one day after administering the therapeutically effective amount of either or both of the immune checkpoint therapy and the DDRi, or administering the therapeutically effective amount of either or both of the immune checkpoint therapy and the DDRi is performed at least one day after administering the therapeutically effective amount of the radiolabeled antibody against DR5.

2. The method of claim 1, wherein the cancer is a solid cancer.

3. The method of claim 2, wherein the solid cancer is breast cancer, triple negative breast cancer, ovarian cancer, or prostate cancer.

4. The method of claim 3, wherein the subject possesses a deleterious BRCA1/2 mutation.

5. The method of claim 1, wherein the radiolabel is $^{225}$Ac, and the therapeutically effective amount of the $^{225}$Ac radiolabeled antibody against DR5 comprises a radiation dose of 0.1 to 10 uCi/kg body weight of the subject, and a protein dose of 0.1 mg/kg to 16 mg/kg body weight of the subject.

6. The method of claim 1, wherein the radiolabel is $^{177}$Lu, and the therapeutically effective amount of the $^{177}$Lu radiolabeled antibody against DR5 comprises a radiation dose of 10 mCi to 500 mCi, and a protein dose of 0.1 mg/kg to 16 mg/kg body weight of the subject.

7. The method of claim 1, wherein the radiolabel is $^{131}$I, and the therapeutically effective amount of the $^{131}$I radiolabeled antibody against DR5 comprises a radiation dose of 10 mCi to 200 mCi, and a protein dose of 0.1 mg/kg to 16 mg/kg body weight of the subject.

8. The method of claim 1, wherein the radiolabeled antibody against DR5 comprises an antibody against DR5 selected from mapatumumab, conatumumab, lexatumumab, tigatuzumab, drozitumab, and LBY-135, or comprises a DR5-binding antibody fragment of any of said antibodies against DR5.

9. The method of claim 5, wherein the $^{225}$Ac radiolabeled antibody against DR5 comprises mapatumumab, or a DR5-binding fragment thereof.

10. The method of claim 5, wherein the $^{225}$Ac radiolabeled antibody against DR5 comprises conatumumab, or a DR5-binding fragment thereof.

11. The method of claim 5, wherein the $^{225}$Ac radiolabeled antibody against DR5 comprises lexatumumab, or a DR5-binding fragment thereof.

12. The method of claim 5, wherein the $^{225}$Ac radiolabeled antibody against DR5 comprises tigatuzumab, or a DR5-binding fragment thereof.

13. The method of claim 5, wherein the $^{225}$Ac radiolabeled antibody against DR5 comprises drozitumab, or a DR5-binding fragment thereof.

14. The method of claim 5, wherein the $^{225}$Ac radiolabeled antibody against DR5 comprises LBY-135, or a DR5-binding fragment thereof.

* * * * *